(12) United States Patent
Moore

(10) Patent No.: US 10,898,614 B2
(45) Date of Patent: Jan. 26, 2021

(54) TISSUE REPAIR LAMINATES

(71) Applicant: POLYNOVO BIOMATERIALS PTY LIMITED, Port Melbourne (AU)

(72) Inventor: Timothy Graeme Moore, Port Melbourne (AU)

(73) Assignee: POLYNOVO BIOMATERIALS PTY LIMITED, Victoria (AU)

( * ) Notice: Subject to any disclaimer, the term of this patent is extended or adjusted under 35 U.S.C. 154(b) by 0 days.

(21) Appl. No.: 16/625,294

(22) PCT Filed: Dec. 21, 2018

(86) PCT No.: PCT/AU2018/051386
§ 371 (c)(1),
(2) Date: Dec. 20, 2019

(87) PCT Pub. No.: WO2019/119061
PCT Pub. Date: Jun. 27, 2019

(65) Prior Publication Data
US 2020/0368397 A1    Nov. 26, 2020

(30) Foreign Application Priority Data

Dec. 22, 2017  (AU) .............................. 2017905176

(51) Int. Cl.
| | |
|---|---|
| *A61L 27/56* | (2006.01) |
| *A61L 27/58* | (2006.01) |
| *A61L 27/18* | (2006.01) |
| *A61F 2/00* | (2006.01) |

(52) U.S. Cl.
CPC ............... *A61L 27/56* (2013.01); *A61L 27/18* (2013.01); *A61L 27/58* (2013.01); *A61F 2/0063* (2013.01)

(58) Field of Classification Search
CPC ...................................................... A61L 27/56
See application file for complete search history.

(56) References Cited

U.S. PATENT DOCUMENTS

2009/0099600 A1    4/2009   Moore et al.

FOREIGN PATENT DOCUMENTS

| WO | 2005089778 A1 | 9/2005 |
| WO | 2017066822 A1 | 4/2017 |

OTHER PUBLICATIONS

International Search Report and Written Opinion dated Apr. 15, 2019 for corresponding PCT Application No. PCT/AU2018/051386.
Walpoth, B. et al., "Biocompatibility of new biodegradable and nondegradable polymeric membranes", Life Support Systems, 1986, vol. 4, Suppl. 2, pp. 82-84.
Tata!, L. et al., "Theemoplastic biodegradable polyurethanes: The effect chain extender structure on properties and in-votro degradation", Biomaterials, 2007, vol. 28, pp. 5407-5417.

*Primary Examiner* — Matthew W Schall
(74) *Attorney, Agent, or Firm* — Polsinelli PC

(57) ABSTRACT

There are provided tissue repair laminates which promote cellular in-growth but also prevent or mitigate tissue adhesion. The laminates comprise a biodegradable polyurethane foam layer which facilitates cellular infiltration and a polyurethane barrier layer which is non-adhesive to tissue. The laminates resist shrinkage under in vivo conditions and possess desirable mechanical properties. The laminates find use in, for example, the repair of herniated tissue, particularly, but not limited to hernias in the abdominal wall.

37 Claims, 6 Drawing Sheets

TISSUE REPAIR LAMINATES

CROSS-REFERENCE TO RELATED APPLICATIONS

This application is a national stage application (under 35 U.S.C. § 371) of PCT/AU2018/051386, filed Dec. 21, 2018, which claims benefit of Australian Application No. 2017905176, filed Dec. 22, 2017, which are incorporated herein by reference in their entireties.

FIELD

This disclosure relates to tissue repair laminates which promote cellular in-growth but also prevent or mitigate tissue adhesion. The laminates comprise biodegradable polyurethanes and find use in, for example, the repair of herniated tissue, particularly, but not limited to hernias in the abdominal wall.

BACKGROUND

Hernias occur when an organ pushes through a defect in muscle or tissue that holds the organ in place, for example the intestines may break through a weakened area in the abdominal wall. Hernias are most common in the abdominal wall but also occur in other parts of the body such as the upper thigh, groin and navel. Inguinal (groin), hiatal (diaphragm), umbilical, abdominal and incisional hernias are commonly treated by surgical intervention.

Various mesh materials have been proposed to reinforce the abdominal wall and to close abdominal wall defects. In certain procedures, including incisional and umbilical hernia repair, the mesh may come into direct contact with the sensitive abdominal viscera. Postoperative adhesions between the mesh and the intestine—may occur and potentially lead to complications such as intestinal fistulization. As a result, re-operative abdominal surgery is frequently required to repair the complications resulting from the adhesions. Intestinal obstructions due to adhesions result in more than 2000 deaths per year in the United States.

Biodegradable synthetics, non-degradable synthetics and biologics have been investigated as mesh materials. Examples include polypropylene, PTFE, polyester and human or porcine derived dermal matrices. Suitable materials are hemostatic, ideally biodegradable, to minimize or eliminate the need for surgical removal, bind well to the repair site, but conversely do not adhere to surrounding tissues.

Polypropylene based mesh has been used in soft tissue reinforcement and defect closure. However, polypropylene may form postoperative adhesions with the abdominal viscera, such as the intestines, when used in the repair of inguinal hernias and other abdominal wall defects. Further, polypropylene is not biodegradable. Thus, the implant remains in the body, and, if necessary, must be removed surgically following the healing process.

Another material which has been employed to prevent adhesions is an expanded polytetrafluoroethylene material marketed as Gore-Tex®. This material, however, is not hemostatic and is also not biodegradable in the human body. Another material is a mesh barrier of carboxymethylcellulose marketed as Interceed®. This material, however, may not be applied in a blood-rich environment as under such conditions the material quickly loses its barrier function.

Films formed from poly(ethyleneoxide) and polyethylene terephthalate have also been proposed as barrier materials to prevent surgical adhesions.

All meshes produce adhesions when placed adjacent to bowel, but the extent of the adhesions are determined by numerous characteristics of the mesh including pore size, filament structure and surface area. Heavy-weight meshes induce an intense fibrotic reaction which ensures strong adherence to the abdominal wall but also causes dense adhesions. In contrast, microporous materials do not allow tissue in-growth and so have a very low risk of adhesion formation, but are unable to adhere strongly to the abdominal wall.

These two extremes illustrate the difficulty of producing a mesh which will adhere well to the abdominal wall but not to the bowel. To alleviate these drawbacks, it has been proposed to cover the tissue infiltratable mesh with an adhesion resistant barrier. The so-formed composite material is surgically placed so that the barrier isolates the sensitive viscera from the porous mesh, preventing the formation of postoperative adhesions. However, covering a sheet of tissue infiltratable mesh with a barrier layer may compromise the tissue infiltratability of the prosthesis.

Another problem with many existing materials is the contraction in use which occurs due to development of scar tissue formed around the mesh.

Accordingly, there is a need for an improved tissue repair device for the repair of tissue or muscle wall defects that exhibits acceptable tissue in-growth properties yet is resistant to adhesion to sensitive organs or tissues. There is a further need for such devices to be biodegradable and to resist contraction in use.

The reference in this specification to any prior publication (or information derived from it), or to any matter which is known, is not, and should not be taken as an acknowledgement or admission or any form of suggestion that the prior publication (or information derived from it) or known matter forms part of the common general knowledge in the field of endeavour to which this specification relates.

SUMMARY

In a first aspect the present disclosure provides a tissue repair laminate comprising:
  (a) a biodegradable polyurethane foam layer having first and second oppositely facing major surfaces; and
  (b) a polyurethane barrier layer having first and second oppositely facing major surfaces;
wherein the first major surface of said barrier layer and the second major surface of said foam layer face each other;
wherein said foam layer comprises a pore structure configured for cellular infiltration; and
wherein the second major surface of said barrier layer is less adhesiogenic than the first major surface of said foam layer.

In a second aspect the present disclosure provides a tissue repair laminate comprising:
  (a) a biodegradable polyurethane foam layer having first and second oppositely facing major surfaces; and
  (b) a polyurethane barrier layer having first and second oppositely facing major surfaces;
wherein the first major surface of said barrier layer and the second major surface of said foam layer face each other;
wherein said foam layer comprises a pore structure configured for cellular infiltration; and
wherein the second major surface of said barrier layer is less adherent to tissue than the first major surface of said foam layer.

In a third aspect the present disclosure provides a tissue repair laminate comprising:
- (a) a biodegradable polyurethane foam layer having first and second oppositely facing major surfaces; and
- (b) a polyurethane barrier layer having first and second oppositely facing major surfaces;

wherein the first major surface of said barrier layer and the second major surface of said foam layer face each other;
wherein said foam layer comprises a pore structure configured for cellular infiltration; and
wherein the second major surface of said barrier layer is substantially non-adherent to tissue.

In a fourth aspect the present disclosure provides a tissue repair laminate comprising:
- (a) a biodegradable polyurethane foam layer having first and second oppositely facing major surfaces; and
- (b) a polyurethane barrier layer having first and second oppositely facing major surfaces;

wherein the first major surface of said barrier layer and the second major surface of said foam layer face each other;
wherein said foam layer comprises a pore structure configured for cellular infiltration; and
wherein the second major surface of said barrier layer is substantially non-adhesiogenic.

In a fifth aspect the present disclosure provides a tissue repair laminate comprising:
- (a) a biodegradable polyurethane foam layer having first and second oppositely facing major surfaces; and
- (b) a polyurethane barrier layer having first and second oppositely facing major surfaces;

wherein the first major surface of said barrier layer and the second major surface of said foam layer face each other;
wherein said foam layer comprises a pore structure configured for cellular infiltration; and
wherein the second major surface of said barrier layer is substantially smooth.

In use, the first major surface of the foam layer is wound facing and the second major surface of the barrier layer is cavity facing.

The tissue repair laminates are advantageous as, in use, the first major surface of the foam layer may be positioned to face, for example, the abdominal wall and the second major surface of the barrier layer exposed to internal organs. The barrier layer surface facing the internal organs substantially resists adherence, whereas the foam layer surface facing, for example, the abdominal wall may adhere to tissue and facilitate tissue regeneration, for example, abdominal wall regeneration.

The tissue repair laminates of the present disclosure may possess one or more of the following advantages including:
- the laminates are substantially resistant to contraction in vivo;
- the laminates limit the incidence of post-operative adhesions arising from the repair of tissue;
- the foam layer enables tissue integration;
- the barrier layer may be rendered substantially non-adherent to tissue during laminate manufacture;
- the barrier layer substantially resists adhesion for long time periods in vivo;
- the laminates have high mechanical strength compared to foam layers alone;
- the laminates are synthetic and not biologic;
- the manufacturing process of the laminates does not substantially affect the tissue ingrowth ability of the foam layer; and
- the foam layer or the laminate may degrade over time so that it need not be surgically removed.

The foam layer may comprise a thermoset polyurethane or may comprise a thermoplastic polyurethane. Preferably the foam layer comprises a thermoset polyurethane. Preferably the foam layer comprises a cross-linked polyurethane.

The barrier layer may comprise a thermoset polyurethane or may comprise a thermoplastic polyurethane. Preferably the barrier layer comprises a thermoplastic polyurethane.

The barrier layer may comprise a biodegradable polyurethane or a non-degradable polyurethane. Preferably, the barrier layer comprises a biodegradable polyurethane. The barrier layer may be designed to degrade at a different rate to the foam layer or at substantially the same rate.

As used herein, the term 'biodegradable' refers generally to the capability of being broken down in the normal functioning of living organisms/tissue, preferably into innocuous, non-toxic or biocompatible products.

In some embodiments the foam layer may degrade faster than the barrier layer.

The tissue repair laminate may comprise any one or more of the following features:
- (i) a suture retention strength of greater than 20 N, or greater than 25 N or greater than 30 N or greater than 35 N
- (ii) an ultimate tensile strength of greater than 20 N/cm, or greater than 25 N/cm, or greater than 30 N/cm, or greater than 35 N/cm or greater than 40 N/cm
- (iii) a ball burst strength of greater than 100 N/cm, or greater than 125 N/cm, or greater than 150 N/cm, or greater than 175 N/cm, or greater than 200 N/cm
- (iv) a tear resistance of greater than 10 N, or greater than 15 N or greater than 20 N.

The tissue repair laminate may shrink less than 20%, or less than 15%, or less than 10%, or less than 5%, independently, in any single surface area, after 10 days under in vivo conditions.

The tissue repair laminate may shrink less than 20%, or less than 15%, or less than 10%, or less than 5%, independently, in any single surface area, after 20 days under in vivo conditions or after 60 days under in vivo conditions, or after 90 days under in vivo conditions, or after 120 days under in vivo conditions, or after 200 days under in vivo conditions, or after 1 year under in vivo conditions, or after 2 years under in vivo conditions.

The foam layer may have a thickness between about 0.1 mm and about 10 mm, or between about 0.2 mm and about 5 mm, or between about 0.3 mm and about 3 mm, or between about 0.3 mm and about 2 mm, or between about 0.4 mm and about 2 mm. The foam layer may have thickness of less than about 10 mm, or less than about 6 mm, or less than about 4 mm, or less than about 2 mm, or less than about 1 mm, or less than about 0.5 mm.

Preferably, the foam layer has a thickness of between 0.3 mm and about 3 mm.

The barrier layer may have a thickness between about 20 µm and about 1000 µm, or between about 50 µm and about 500 µm, or between about 50 µm and about 400 µm.

In some embodiments the foam layer has a thickness between about 0.3 mm and about 3 mm and the barrier layer has a thickness between about 50 µm and about 400 µm.

In some embodiments the foam layer has a thickness between about 0.3 mm and about 2 mm and the barrier layer has a thickness between about 100 µm and about 300 µm.

In some embodiments the foam layer has a thickness between about 0.3 mm and about 1 mm and the barrier layer has a thickness between about 100 µm and about 300 µm.

In some embodiments the foam may be a non-reticulated foam. In some embodiments the foam may be a reticulated foam. The foam may, preferably, have interconnecting pores. Preferably the foam is a non-reticulated foam.

As used herein the term 'non-reticulated' polyurethane foam refers to a polyurethane foam which has not been subjected to a post manufacturing step to remove cell windows using either chemicals (such as alkaline solution), heat (such as controlled combustion of hydrogen and oxygen), or solvents.

In some embodiments the foam may have a density between 3 g/100 ml and 12 g/100 ml, or between 4 g/100 ml and 10 g/100 ml, or between 5 g/100 ml and 8 g/100 ml.

In some embodiments the porosity of the foam may be greater than 50%, or greater than 75%, or from 80 to 95%, or from 95 to 99.9%. It is desirable that the porosity should be as high as possible while maintaining other mechanical specifications. If the porosity is too low the pores may not interconnect. If the porosity is too high the structural integrity of the foam may be mechanically compromised.

In some embodiments the average pore size of the foams may be greater than 50 µm, or greater than 75 µm, or greater than 100 µm, or greater than 200 µm, or in the range 100 to 600 µm, or in the range 100 to 400 µm.

In some embodiments the average pore size of the foam is in the range 50 to 600 µm, or in the range 60 to 600 µm, or in the range 70 to 600 µm, or in the range 75 to 400 µm, or in the range 75 to 300 µm, or in the range 100 to 300 µm.

Preferably the average pore size of the foam is greater than 75 µm, more preferably between 100 and 300 µm.

In some embodiments the tissue repair laminate may have a weight between 50 and 800 g/m$^2$, or between 100 and 600 g/m$^2$, or between 200 and 500 g/m$^2$.

In some embodiments of any of the herein disclosed aspects the second major surface of the barrier layer is substantially non-adherent to tissue.

By substantially non-adherent it is meant, in some embodiments, that the barrier layer either does not adhere to tissue or only adheres such that it can be easily released from tissue without damage to the tissue.

In some embodiments of any of the herein disclosed aspects the second major surface of the barrier layer has a higher surface smoothness than the first major surface of the foam layer. As used herein, the term 'smooth', in relation to a surface, means that the surface is substantially non-adherent to tissue.

In some embodiments the first major surface of the foam layer and the second major surface of the barrier layer are in direct contact with each other. In some embodiments the first major surface of the foam layer and the second major surface of the barrier layer are fused to each other.

In some embodiments the laminate may comprise one or more further layers disposed between the foam layer and the barrier layer. The one or more further layers may be an adhesive layer.

Foam Layer

The biodegradable polyurethane foam layer may be biodegradable within a living organism to biocompatible degradation products.

The polyurethane foam layer may be in vivo degradable. The polyurethane foam layer may be degradable at temperatures between about 35° C. and about 42° C.

The polyurethane foam layer may degrade by hydrolysis. The polyurethane foam layer may degrade by hydrolysis of ester functionalities.

Foam Layer Polyols

The polyurethane foam may be derived from one or more biodegradable polyols and one or more isocyanates. Alternatively, the polyurethane foam may be derived from a mixture of one or more biodegradable polyols and one or more non-biodegradable polyols and one or more isocyanates. Preferably the biodegradable polyols are polyester polyols.

The foam may be derived from one or more biodegradable polyols having a molecular weight of less than or equal to about 2000 Daltons, or less than or equal to about 1500 Daltons, or less than or equal to about 1300 Daltons.

The biodegradable polyols may have a molecular weight between about 200 and about 2,000 Daltons, or between about 200 and about 1,500 Daltons, or between about 200 and about 1,300 Daltons, or between about 600 and about 1500 Daltons, or between about 900 and about 1300 Daltons.

The biodegradable polyols may have a molecular weight of less than or equal to about 10,000 Daltons, or less than or equal to about 8,000 Daltons, or less than or equal to about 6,000 Daltons, or less than or equal to about 4,000 Daltons, or less than or equal to about 2,000 Daltons, or less than or equal to about 1,500 Daltons, or less than or equal to about 1,000 Daltons, or less than or equal to about 800 Daltons, or less than or equal to about 600 Daltons, or less than or equal to about 500 Daltons, or less than or equal to about 400 Daltons, or less than or equal to about 350 Daltons, or less than or equal to about 300 Daltons.

The biodegradable polyols may have a molecular weight of less than 500 Daltons or less than 400 Daltons or less than 350 Daltons, or less than 300 Daltons.

The biodegradable polyols may be in the liquid state at 20° C. and atmospheric pressure. Alternatively, the biodegradable polyols may be in the solid state at 20° C. and atmospheric pressure. In some embodiments the polyols may in the form of a mixture of solid and liquid at 20° C.

The biodegradable polyols may be derived from one or more polyol initiators and one or more hydroxy acids, diacids or cyclic esters and combinations thereof.

In some embodiments the biodegradable polyol may be derived from one or more polyol initiators and at least one hydroxy acid.

In some embodiments the biodegradable polyol may be derived from one or more polyol initiators and at least one diacid.

In some embodiments the biodegradable polyol may be derived from one or more polyol initiators and at least one cyclic ester.

In some embodiments the biodegradable polyol may be derived from one or more polyol initiators, at least one hydroxy acid and at least one diacid.

In some embodiments the biodegradable polyol may be derived from one or more polyol initiators, at least one hydroxy acid and at least one cyclic ester.

In some embodiments the biodegradable polyol may be derived from one or more polyol initiators, at least one diacid and at least one cyclic ester.

In some embodiments the biodegradable polyol may be derived from one or more polyol initiators, at least one hydroxyl acid, at least one diacid and at least one cyclic ester.

The one or more polyol initiators may be pentaerythritol, trimethylol propane, glycerol, 1,4-butanediol, ethylene glycol, sorbitol, glucose, sucrose, 1,2-propanediol, 1,3-propanediol, pentane diol, myoinositol, hexamethylenediol, heptanediol, octanediol, nonanediol, decanediol, dodecanediol, 2-ethyl-1,3-hexanediol (EHD), 2,2,4-trimethyl pentane-1,3-diol (TMPD), 1,4-cyclohexane dimethanol, diethylene glycol, dipropylene glycol, and combinations thereof.

Non-limiting examples of hydroxy acids include l-lactic acid, d-lactic acid, d,l-lactic acid, mandelic acid, phenyl-lactic acid, hydroxybutyric acid, hydroxyvaleric acid or glycolic acid and combinations thereof.

Non-limiting examples of cyclic esters include ε-caprolactone, glycolide, lactide, mandelide, and ρ-dioxanone and combinations thereof. The biodegradable polyols may be prepared via a ring-opening polymerisation reaction or a condensation reaction.

Non-limiting examples of diacids include oxalic acid, malonic acid, succinic acid, glutaric acid, adipic acid, pimelic acid, suberic acid, azelaic acid, sebacic acid, undecanedioic acid, dodecanedioic acid, tridecanedioic acid, and hexadecanedioic acid and combinations thereof.

The biodegradable polyols may be prepared via a ring-opening polymerisation reaction or a condensation reaction or via both a ring-opening polymerisation reaction and a condensation reaction.

The one or more non-biodegradable polyols may be a polyether polyol. The polyether polyol may be one or more of glycerol ethoxylate, glycerol propoxylate, glycerol ethoxylate-co-propoxylate, glycerol ethoxylate-block-propoxylate, pentaerythritol ethoxylate, pentaerythritol propoxylate and trimethylolpropane propoxylate.

The one or more non-biodegradable polyols may have a molecular weight of less than or equal to about 2000 Daltons, or less than or equal to about 1500 Daltons, or less than or equal to about 1300 Daltons.

The non-biodegradable polyols may have a molecular weight between about 200 and about 2,000 Daltons, or between about 200 and about 1,500 Daltons, or between about 200 and about 1,300 Daltons, or between about 600 and about 1500 Daltons, or between about 900 and about 1300 Daltons.

The non-biodegradable polyols may have a molecular weight of less than or equal to about 10,000 Daltons, or less than or equal to about 8,000 Daltons, or less than or equal to about 6,000 Daltons, or less than or equal to about 4,000 Daltons, or less than or equal to about 2,000 Daltons, or less than or equal to about 1,500 Daltons, or less than or equal to about 1,000 Daltons, or less than or equal to about 800 Daltons, or less than or equal to about 600 Daltons, or less than or equal to about 500 Daltons, or less than or equal to about 400 Daltons, or less than or equal to about 350 Daltons, or less than or equal to about 300 Daltons.

The non-biodegradable polyols may have a molecular weight of less than 500 Daltons or less than 400 Daltons or less than 350 Daltons, or less than 300 Daltons.

The biodegradable polyols impart biodegradability to the foam. The polyols may be prepared by condensation polymerization or ring-opening polymerization with a high proportion of initiator (or starter) to control the molecular weight. The amount of initiator may range from between 1 mole of initiator per 200 g of polyol and 1 mole of initiator per 5000 g of polyol, or between 1 mole of initiator per 500 g polyol and 1 mole of initiator per 2000 g of polyol. Non-limiting examples of suitable monomers for the initiator include pentaerythritol (4-arm), trimethylol propane (3-arm), glycerol (3-arm), 1,4-butanediol (2-arm), myo-inositol (6-arm). Mixtures of initiators may be utilized. Mixtures of polyols may be utilized. It may be preferable to minimize the number of components. However, in some instances it may be advantageous to utilise more than one polyol, or more than two. The polyol may have a hydroxyl functionality of 2 or more. Polyols having only a single hydroxyl functionality, when used in large amounts, may not result in an adequate foam. However, minor amounts may be used to adjust the properties of the foam, for example, adding a few percent of a mono-hydroxyl compound which has a long-chain lipophilic chain, may influence the hydrophobicity/hydrophilicity of the foam.

The rate of degradation of the foam layer may be controlled by altering the ratio of biodegradable polyol to that of non-biodegradable polyol. By reducing or eliminating a non-biodegradable polyol from the formulation, faster degrading foam layers may be produced which may be desirable in certain applications. Monomer selection may also influence the rate of degradation due to kinetic differences in the rate of hydrolysis of different ester linkages.

Biodegradable and non-biodegradable polyols have different functions in the foam layer of the tissue repair laminate. Non-biodegradable polyols may be selected from the polyether polyols, for example, glycerol ethoxylate, glycerol propoxylate and glycerol ethoxylate-co-propoxylate. Such non-biodegradable polyols may stabilize the foam through the introduction of non-biodegradable function. Further they may provide a mechanism to control the hydrophilic/hydrophobic balance through, for example, the ethoxylate/propoxylate content. They may also improve foam resilience by lowering the glass transition temperature ($T_g$).

Biodegradable polyols may be solid at lower molecular weights than non-biodegradable polyols, for example, polycaprolactone diol of 500 molecular weight is a solid at room temperature, whereas poly(propylene glycol) remains a liquid to a much higher molecular weight. High molecular weight non-biodegradable liquid polyols may act as a 'filler' to reduce the isocyanate content and hence reduce the likelihood of scorching through excessive exothermic reaction during preparation of the foams.

Biodegradable polyols may be derived from one or more polyol initiators and at least one hydroxy acid and/or cyclic ester. They may contribute to lowering the $T_g$ in circumstances where the $T_g$ has not been reduced sufficiently by the non-biodegradable polyether. The polyol may be a 3-arm, glycerol-initiated polyol based on ε-caprolactone and one of glycolic acid or lactic acid. The amount of the CL:(LA and/or GA) may influence both the glass transition as well as the degradation time. More caprolactone lowers the $T_g$ and increases the degradation time. The molecular weight may be 800-1200 Daltons. The molecular weight may be low enough to be liquid, but high enough to not require high amounts of isocyanate for reaction in order to avoid scorching.

Foam Layer Isocyanates

The polyurethanes from which the foam layer is prepared may be derived from one or more biodegradable polyols and one or more isocyanates. The molar ratio of isocyanate functions to hydroxy and other isocyanate reactive functions from which the foam is derived (the isocyanate index) may be less than or equal to 1.0, or less than or equal to 0.9, or less than or equal to 0.8, or less than or equal to 0.7, or less than or equal to 0.6. The isocyanate index may be between 0.4 and 1.0, or between 0.6 and 0.9.

The polyurethane foam may be derived from polyols and isocyanates having an isocyanate content (that is, the content of NCO functions) of less than 20% by weight, or less than 19%, or less than 18%, or less than 17%, or less than 16%, or less than 15%, or less than 14%, or less than 13%, or less than 12%, or less than 11%, or less than 10%, or less than 9%, or less than 8% by weight based on the total weight of polyols and isocyanates. The foam may have an isocyanate content of between 5% and 20%, or between 8% and 17%, or between 11% and 14% by weight based on the total weight of polyol and isocyanate.

The degradation products from aliphatic isocyanates (such as ethyl lysine diisocyanate (ELDI)) are generally considered to be more biocompatible than the degradation products from aromatic diisocyanates. Accordingly, isocyanates such as hexamethylene diisocyanate (HDI) and ELDI may be particularly suitable. Isophorone diisocyanate (IPDI) may also be used but may impart a higher glass transition temperature which may result in a stiffening of the foam. Combinations of isocyanates may be used and may in some instances be preferable, for example, glass transition can be adjusted by combinations of HDI and IPDI. Trimethylhexamethylenediisocyanate, 1,4-butane diisocyanate, methyllysine diisocyanate (MLDI) and other isocyanates commonly used in polyurethane synthesis may also be suitable.

Lowering the isocyanate index results in softer and weaker foam layers which degrade more quickly. Increasing the isocyanate index may increase the degradation time but results in stronger foam layers.

A biodegradable polyurethane foam is advantageous since it may be designed to include the properties of resilience, resistance to premature degradation, resistance to contraction, prevention of excessive acidic degradation products, biocompatibility, controlled water absorption, compatibility with other polyurethane layers and ease of incorporating additives during synthesis. The foams may be soft and conformable to a desired shape.

The foams may be designed to degrade at a specific rate. They may be designed to retain structural integrity for over, for example, three months or they may be designed to retain structural integrity for as little as, for example, a few days, even one or two days.

The polyurethane foam layer may degrade, under the conditions of ASTM F1635, such that the mass of the foam layer decreases by between about 10% and about 90% in a period of one year or less.

Alternatively, the mass of the foam layer may decrease by between about 10% and about 90% in a period of eleven months or less, or ten months or less, or nine months or less, or eight months or less, or seven months or less, or six months or less, or five months or less, or four months or less, or three months or less, or two months or less, or one month or less.

The rate of degradation, under the conditions of ASTM F1635, may be controlled through varying the nature and ratios of the components of the polyurethane. Accordingly, the polyurethane may be designed to degrade within a specific period of time. This is advantageous in providing materials that are partially, fully, or substantially fully degradable in a specific period of time, for example, when the functional aspects of the polyurethane foam layer are no longer required.

This is particularly useful where the polyurethane is targeted for in vivo applications as the polyurethane may not need to be surgically removed from a patient's body.

The rate of degradation of the foam may be controlled by altering the ratio of biodegradable polyol to non-biodegradable polyol or through choice of monomers. By reducing or eliminating a non-biodegradable polyol from the formulation, faster degrading materials may be produced which may be desirable in certain applications.

The foams may be derived from at least one prepolymer which may be prepared by contacting one or more biodegradable polyols and/or one or more polyol initiators with one or more polyisocyanates. Non-limiting examples of polyol initiators are, for example, pentaerythritol, trimethylol propane, glycerol, 1,4-butanediol and myo-inositol, ethylene glycol, sorbitol, glucose, sucrose, 1,2-propanediol and mixtures thereof. The foam may be derived from a mixture of such so-formed prepolymers and further polyisocyanate. The foam may contain less than 50% by weight of prepolymer and greater than 50% by weight of polyisocyanate based on the combined weight of these components. The foam may contain from less than 30% by weight of prepolymer and greater than 70% by weight of polyisocyanate based on the combined weight of these components. Foams prepared in this way advantageously may possess high strength and fine cell structure.

The foam may be derived from a biodegradable polyol having a molecular weight less than or equal to about 1300 Dalton and from polyols and polyisocyanates having an isocyanate (NCO) content of less than 20%, or less than 19%, or less than 18%, or less than 17%, or less than 16%, or less than 15%, or less than 14%, or less than 13%, or less than 12%, or less than 11%, or less than 10%, or less than 9%, or less than 8% by weight based on the total weight of polyols and polyisocyanates.

The foam may be derived from a biodegradable polyol and a non-biodegradable polyol wherein the molecular weight of the biodegradable polyol is less than our equal to about 1300 Dalton and from polyols and polyisocyanates having an isocyanate (NCO) content is less than 20%, or less than 19%, or less than 18%, or less than 17%, or less than 16%, or less than 15%, or less than 14%, or less than 13%, or less than 12%, or less than 11%, or less than 10%, or less than 9%, or less than 8% by weight based on the total weight of polyols and polyisocyanates.

The foam may be derived from a biodegradable polyol having a molecular weight less than or equal to about 1300 Dalton and from polyols and polyisocyanates having an isocyanate (NCO) content of less than 20%, or less than 19%, or less than 18%, or less than 17%, or less than 16%, or less than 15%, or less than 14%, or less than 13%, or less than 12%, or less than 11%, or less than 10%, or less than 9%, or less than 8% by weight based on the total weight of polyols and polyisocyanates and a molar ratio of isocyanate functions to hydroxy and other isocyanate reactive functions (the isocyanate index) less than or equal to 1.0.

The foam may be derived from a biodegradable polyol and a non-biodegradable polyol wherein the molecular weight of the biodegradable polyol is less than our equal to about 1300 Dalton and from polyols and polyisocyanates having an isocyanate (NCO) content is less than 20%, or less than 19%, or less than 18%, or less than 17%, or less than 16%, or less than 15%, or less than 14%, or less than 13%, or less than 12%, or less than 11%, or less than 10%, or less than 9%, or less than 8% by weight based on the total weight of polyols and polyisocyanates and a molar ratio of isocyanate functions to hydroxy and other isocyanate reactive functions (the isocyanate index) less than or equal to 1.0.

Various additives known in the fields of polyurethane foam technology and tissue engineering may be added to the foam. These additives may be added during or after synthesis of the foam. The additives in some cases may react during the foam synthesis and be incorporated covalently into the foam. Exemplary additives include antimicrobial agents, plasticizers, pore openers, antioxidants, antistatic agents, catalysts, fillers, flame retardants, softeners/flexibilisers, cell control agents, release agents, stabilizers, fillers, dyes, pigments, pigment dispersants, solvents, anaesthetics, cells, enzymes, proteins, growth factors, growth inhibitors, haemostatic agents and bioactive agents such as drugs. The additives may or may not be chemically bonded to the foam.

Catalysts

There are a large number of catalysts known in the field of polyurethane synthesis that may be used in the preparation of the polyurethanes of the present disclosure. Various catalysts may be used in the preparation of the compositions and these may provide different attributes. For example, dibutyltin dilaurate (DBTL), stannous octoate and amine-based catalysts, such as DABCO. Bismuth, zinc and titanium-based catalysts are also known to catalyze urethane formation effectively and exhibit low toxicity. COSCAT Z-22 is a zinc-based catalyst and is an example of a catalyst that can be used that has low toxicity and gives effective results. Mercury and lead-containing catalysts are effective but are considered toxic (non-biocompatible) and therefore unsuitable. Combinations of catalysts are known to be effective. Minimisation of catalyst amount is also desirable.

Surfactant

The function of the surfactant (stabilizer, foaming agent) is to assist in preventing the bubbles in the foam from bursting when they are formed during the reaction, which allows them to rise and create a stable foam which can then cure.

Surfactants may be siloxane-ether copolymers, fluoro-ether copolymers, or other amphiphilic compounds containing a hydrophobic portion and a hydrophilic portion. There are many commercial surfactants that have been specifically developed for polyurethane foams. Amounts used vary from 0.01% to 1.5% by mass of the overall formulation. Preferred amounts are in the range 0.01% to 0.20% of the formulation. The most suitable amount depends on the molecular weight of the surfactant and the composition and type, as well as the remainder of the formulation—some formulations may be more hydrophobic and some may be more hydrophilic and hence may require different amounts of stabilisation. Useful surfactants may be simple block copolymers and brush-type copolymers. It is straightforward for the skilled person to vary the concentration of surfactant and determine which concentration is most effective in stabilizing the foam layer.

Blowing Agent

The foams may be blown by any method known in the art. The blowing agent may be generated during formation of the foam and/or may be added as one or more further components. Water may be used in the formulation to react with isocyanate, thus forming a urea linkage and $CO_2$ gas. The $CO_2$ gas creates the bubbles and blows the foam. Temperature, mixing and choice of surfactant, for example, may all affect the size of the bubbles (cell size). Commercially, polyurethane foams range in pore size from microporous (low density shoe soles) through to open cell large-celled foams (for example in filters or foam mattresses). Desirable porosities may be obtained by using 0.1 to 4% by weight of water, preferably 1.0 to 1.5% by weight of water in the overall formulation. This results in an appropriate level of foaming. Less water results in a denser foam. Higher amounts of water may be useful, but there will be a limit where the mechanical properties are negatively affected and scorching becomes likely.

Pentane and other low-boiling hydrocarbons may also be suitable as blowing agents. Foams produced in this manner may be advantageously urea-free due to the absence of water. Desirably, the absence of water reduces the amount of isocyanate required to react in the formulation, which consequently reduces the amount of heat generated when the foam is produced. This is particularly advantageous in large scale preparations where the heat of reaction may be more difficult to dissipate from the foam.

The foam layer may comprise any one or more of the herein disclosed features in any combination.

Preparation of the Foam Layer Polyurethane

The foams may be simply prepared by a one-pot method. All the components may be combined and mixed with or without the application of heat, and the foam will rise and cure. Alternatively, the foams may be prepared by any of the continuous or semi-continuous processes well known in the art.

In one embodiment, one or more polyols or polyol initiators is/are first treated with a polyisocyanate to form a prepolymer. This prepolymer is in turn treated with further components so to form the foam. In another embodiment, further polyisocyanate over and above that utilized to form the prepolymer may be utilized.

In another embodiment, all components, apart from the polyisocyanate component(s) are mixed together to form one part. The polyisocyanate is then added so as to begin the reaction. This is advantageous in that the two parts are both stable prior to mixing them together.

The foam may be prepared in a solvent free process.

The foams may be advantageously prepared by a one-pot batch procedure which may require no isolation or purification of intermediate materials. The foams may be prepared from low cost raw materials.

Reticulation

In some instances it may be advantageous to reticulate the foam. Reticulation results in the removal of cell windows so as to increase the amount of open cell material. This may be advantageous when fluid transfer is a requirement. This may be performed in a special chamber (reticulation chamber) where hydrogen and oxygen are introduced to the foam and ignited to disrupt and remove any cell windows.

Cell openers or cell opening agents may be added to the foam mixture to, for example, disrupt the pore structure during the foaming process, thereby creating foams with a natural sponge structure. Cell openers may reduce the tightness and shrinkage of the foam, resulting in dimensionally stable foams with inter-connected pores. Cell openers and other reaction components of polyurethane foams are discussed, for example in Szycher, M, Szycher's Handbook of Polyurethanes, CRC Press, New York, N.Y., 9-6 to 9-8 (1999). Cell openers suitable for use include powdered divalent metal salts of long-chain fatty acids having from about 1-22 carbon atoms. Divalent metal salts of stearic acid, such as calcium and magnesium stearate, are examples of cell openers. The concentrations of cell openers in the resin mix may be in the range of approximately 0.1-7.0% by weight or in the range of approximately 0.3 to 1% by weight.

Bioactive Agents

Bioactive agents may optionally be added to the foam mix. As used herein, the term 'bioactive' refers generally to an agent, a molecule, or a compound that affects biological or chemical events in a host.

Barrier Layer

The barrier layer of the presently disclosed tissue repair laminate may be substantially resistant to adhesion to sensitive tissues and organs. The barrier lay may be non-adhesiogenic or substantially non-adhesiogenic.

The barrier layer may consist of more than one layer. For example, the barrier layer may be a laminate of two or more sheets of the same or different polyurethanes.

In some embodiments the barrier layer polyurethane comprises an oriented polyurethane.

In some embodiments the oriented polyurethane comprises a biaxially oriented polyurethane.

In some embodiments the oriented polyurethane is annealed.

The barrier layer should be flexible enough to conform to the shape of the foam layer. The barrier layer may be composed of one or more layers of polyurethane.

The barrier layer may be biodegradable or non-biodegradable but should preferably be biocompatible.

The barrier layer may be a thermoformed sheet.

The barrier layer may be formed by melt pressing.

The barrier layer may be formed by casting a film.

The barrier layer may be subjected to orientation either in one direction or in two directions.

The barrier layer provides strength to the tissue repair laminate. In a preferred embodiment an oriented barrier layer provides high strength to the tissue repair laminate.

The barrier layer may be a woven or non-woven layer of fibres which prevents tissue adhesion, as may be obtained for example by electrospinning.

Barrier layers of 50-400 μm thickness offer a good balance between strength (increases with thickness), permeability (decreases with thickness) and handling (stiffer as it gets thicker). Additionally, the mass of the barrier layer may become too high compared to the mass of the foam layer if it is too thick.

The tissue repair laminate may comprise a biocompatible and/or biodegradable adhesive located between the foam layer and the barrier layer.

In other embodiments, no adhesive may be utilised and the barrier layer may be melted directly onto the foam layer.

Barrier Layer Polyurethane

The barrier layer may comprise a biodegradable polyurethane. The barrier layer may be derived from one or more polyols, one or more isocyanates and one or more chain extenders. The chain extenders may be biodegradable or non-degradable, preferably the chain extenders comprise biodegradable chain extenders.

The barrier layer polyurethane may be derived from: one or more chain extenders represented by formula (1) or formula (2)

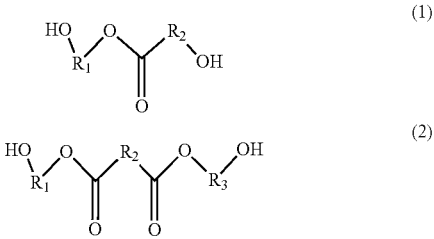

wherein $R_1$, $R_2$ and $R_3$ are independently selected from optionally substituted $C_{1-20}$ alkylene and optionally substituted $C_{2-20}$ alkenylene;
one or more aliphatic polyester polyols; and
one or more aliphatic diisocyanates.

The barrier layer polyurethane may have a number average molecular weight ($M_w$) up to 200,000 Daltons, or up to 150,000 Daltons, or up to 100,000 Daltons, or up to 60,000 Daltons, or up to 40,000 Daltons, or up to 20,000 Daltons.

The barrier layer polyurethane may have a number average molecular weight ($M_w$) between 2,000 and 200,000 Daltons, or between 5,000 and 150,000 Daltons or between 10,000 and 100,000 Daltons or between 20,000 and 100,000 Daltons or between 2,000 and 60,000 Daltons, or between 2,000 and 40,000 Daltons or between 2,000 and 20,000 Daltons.

The polyurethane may have a number average molecular weight ($M_n$) up to 100,000 Daltons, or up to 75,000 Daltons, or up to 50,000 Daltons, or up to 30,000 Daltons, or up to 20,000 Daltons, or up to 10,000 Daltons. Preferably, the number average molecular weight of the polyurethane is between 50,000 and 100,000 Daltons.

The polyurethane may have a polydispersity ($M_w/M_n$) between 1.0 and 4.0, or between 1.0 and 3.5, or between 1.5 and 3.0. Preferably the polydispersity is between 1.0 and 2.0.

Barrier Layer Polyols

The polyols may comprise one or more polyester polyols.

The polyols may have a molecular weight between about 200 and about 2,000 Daltons, or between about 200 and about 1,500 Daltons, or between about 200 and about 1,300 Daltons.

The polyols may have a molecular weight of less than or equal to about 10,000 Daltons, or less than or equal to about 8,000 Daltons, or less than or equal to about 6,000 Daltons, or less than or equal to about 4,000 Daltons, or less than or equal to about 2,000 Daltons, or less than or equal to about 1,500 Daltons, or less than or equal to about 1,000 Daltons, or less than or equal to about 800 Daltons, or less than or equal to about 600 Daltons, or less than or equal to about 500 Daltons, or less than or equal to about 400 Daltons, or less than or equal to about 350 Daltons, or less than or equal to about 300 Daltons.

The polyols may have a molecular weight of less than 500 Daltons or less than 400 Daltons or less than 350 Daltons, or less than 300 Daltons.

The polyols may be in the liquid state at 20° C. and atmospheric pressure. Alternatively, the polyols may be in the solid state at 20° C. and atmospheric pressure.

The polyols may be derived from one or more diol initiators and one or more hydroxy acids, diacids or cyclic esters and combinations thereof.

In one embodiment the polyol may be derived from one or more diol initiators and at least one hydroxy acid.

In one embodiment the polyol may be derived from one or more diol initiators and at least one diacid.

In one embodiment the polyol may be derived from one or more diol initiators and at least one cyclic ester.

In one embodiment the polyol may be derived from one or more diol initiators, at least one hydroxy acid and at least one diacid.

In one embodiment the polyol may be derived from one or more diol initiators, at least one hydroxy acid and at least one cyclic ester.

In one embodiment the polyol may be derived from one or more diol initiators, at least one diacid and at least one cyclic ester.

In one embodiment the polyol may be derived from one or more diol initiators, at least one hydroxyl acid, at least one diacid and at least one cyclic ester.

Non-limiting examples of the one or more diol initiators include ethylene glycol, 1,3-propanediol, 1,2-propanediol, 1,4-butanediol, pentanediol, hexamethylenediol, heptanediol, octanediol, nonanediol, decanediol, dodecanediol, 2-ethyl-1,3-hexanediol (EHD), 2,2,4-trimethyl pentane-1,3-diol (TMPD), 1,4-cyclohexane dimethanol, diethylene glycol, dipropylene glycol, and combinations thereof. Non-limiting examples of diacids include oxalic acid, malonic acid, succinic acid, glutaric acid, adipic acid, pimelic acid, suberic acid, azelaic acid, sebacic acid, undecanedioic acid, dodecanedioic acid, tridecanedioic acid, and hexadecanedioic acid and combinations thereof. Non-limiting examples of hydroxy acids include 1-lactic acid, d-lactic acid, d,l-lactic acid, mandelic acid, phenyl-lactic acid, hydroxybutyric acid, hydroxyvaleric acid or glycolic acid and combinations thereof. Non-limiting examples of cyclic esters include ε-caprolactone, glycolide, lactide, mandelide, and ρ-dioxanone and combinations thereof. The polyols may be prepared via a ring-opening polymerisation reaction or a condensation reaction or via both a ring-opening polymerisation reaction and a condensation reaction.

Barrier Layer Chain Extenders

In some embodiments R1, R2 and R3 of formulae (1) and (2) are independently selected from optionally substituted C1-6 alkylene and optionally substituted C2-6 alkenylene.

The term "optionally substituted" refers to a group which may or may not be further substituted with one or more groups selected from C1-6 alkyl, C2-6 alkenyl, C2-6 alkynyl, halo, halo C1-6alkyl, halo C2-6 alkenyl, halo C2-6 alkynyl, hydroxy, C1-6 alkoxy, C2-6 alkenyloxy, halo C1-6 alkoxy, haloalkenyloxy, nitro, nitro C1-6 alkyl, nitro C2-6 alkenyl, nitro C-6 alkynyl, nitroheterocyclyl, amino, C1-6 alkylamino, C1-6 dialkylamino, C2-6 alkenylamino, C2-6 alkynylamino, acyl, alkenylacyl, alkynylacyl, acylamino, diacylamino, acyloxy, C1-6 alkylsulphonyloxy, heterocyclyl, heterocyclyloxy, heterocyclylamino, haloheterocyclyl, C1-6 alkylsulphenyl, carboalkoxy, mercapto, C1-6 alkylthio, acylthio, phosphorus-containing groups and the like. Preferred optional substituents are methyl, ethyl, propyl, butyl, and phenyl.

The chain extender of formula (1) or formula (2) is preferably hydroxy-acetic acid 3-hydroxy-propyl ester, 6-hydroxy-hexanoic acid 2-hydroxyethyl ester, 6-hydroxy-hexanoic acid 4-hydroxybutyl ester, ethylene glycol succinic acid diester diol, ethylene glycol fumaric acid diester diol, glycolic acid-ethylene glycol dimer and lactic acid-ethylene glycol dimer; and mixtures thereof.

The chain extender of formula (1) of formula (2) may be prepared from one or more diols and one or more hydroxy acids and/or cyclic esters.

Non-limiting examples of the one or more diols include ethylene glycol, 1,3-propanediol, 1,2-propanediol, 1,4-butanediol, pentanediol, hexamethylenediol, heptanediol, octanediol, nonanediol, decanediol, dodecanediol, 2-ethyl-1,3-hexanediol (EHD), 2,2,4-trimethyl pentane-1,3-diol (TMPD), 1,4-cyclohexane dimethanol, diethylene glycol, dipropylene glycol, and combinations thereof. Non-limiting examples of hydroxy acids include 1-lactic acid, d-lactic acid, d,l-lactic acid, mandelic acid, phenyl-lactic acid, hydroxybutyric acid, hydroxyvaleric acid or glycolic acid and combinations thereof. Non-limiting examples of cyclic esters include ε-caprolactone, glycolide, lactide, mandelide, and ρ-dioxanone and combinations thereof.

The polyurethane may further comprise one or more aliphatic polyol chain extenders which are hydrolytically non-degradable under in vivo conditions. For example, the polyurethane may further comprise one or more diol chain extenders which do not contain ester functionality in their backbones. Preferably, the non-degradable chain extender is an alkane diol having up to 30 carbon atoms, for example, ethylene glycol, 1,3-propanediol, 1,2-propanediol, 1,4-butanediol, pentanediol, hexamethylenediol, heptanediol, nonanediol, dodecanediol, 2-ethyl-1,3-hexanediol (EHD), 2,2,4-trimethyl pentane-1,3-diol (TMPD), 1,6-hexanediol, 1,4-cyclohexane dimethanol, diethylene glycol, dipropylene glycol, and mixtures thereof.

Barrier Layer Diisocyanates

The aliphatic diisocyanate is preferably 4,4'-methylene dicyclohexyl diisocyanate (HMDI), 1,6-hexane diisocyanate (HDI), 1,4-butane diisocyanate (BDI), L-lysine diisocyanate (LDI), ethyl-L-lysine diisocyanate (ELDI), methyl-L-lysine diisocyanate (MLDI), 2,4,4-trimethylhexamethylenediisocyanate, other similar diisocyanates, and mixtures thereof.

The degradation products from aliphatic isocyanates (such as ethyl lysine diisocyanate (ELDI)) are generally considered to be more biocompatible than the degradation products from aromatic diisocyanates. Accordingly, isocyanates such as hexamethylene diisocyanate (HDI) and ELDI may be particularly suitable. Isophorone diisocyanate (IPDI) may also be used. Combinations of isocyanates may be used and may in some instances be preferable—for example, glass transition can be adjusted by combinations of HDI and IPDI. Trimethylhexamethylenediisocyanate, 1,4-butane diisocyanate, methyl-lysine diisocyanate (MLDI) and other isocyanates commonly used in polyurethane synthesis may also be suitable.

Barrier Layer Polyurethane Degradation

The polyurethane may contain hard and soft segments. The ratio of hard to soft segment influences the melting point of the polyurethane.

The hard segment content (% HS) of the polyurethane (that is, the combined content of the components derived from the chain extender of formula (1) or formula (2) and isocyanate, expressed by weight percentage) may range from 2 to 100 wt. %, or from 5 to 80 wt %, or from 10 to 70 wt %.

The soft segment content (% SS) of the polyurethane (that is, the percentage by weight of the components derived from the polyester polyol) may range from 5-98%, and in some embodiments, is at least 25% or at least 40%.

In some embodiments the polyurethane comprises hard and soft segments wherein the hard segment content (% HS) of the polyurethane is less than 60%, preferably between 30 and 60%.

The amount of chain extender of formula (1) or formula (2) in the polyurethane may be varied to vary the non-degradable length of continuous urethane in the hard segment. For example, the non-degradable length of the hard segment may have an average molecular weight between 100 and 10,000 Daltons, or between 200 and 5,000 Daltons, or between 400 and 2,000 Daltons, or between 200 and 700 Daltons or between 320 and 700 Daltons.

The barrier layer polyurethane may degrade, under the conditions of ASTM F1635, such that the number average molecular weight ($M_n$) of the polyurethane decreases and/or the mass of the barrier layer decreases by between 10% and 90% in a period of one year or less.

The barrier layer polyurethane may be in vivo degradable. The polyurethane may be degradable at temperatures between 35 and 42° C.

Alternatively, the number average molecular weight ($M_n$) of the polyurethane may decrease and/or the mass of the barrier layer may decrease by between 10% and 90% in a period of eleven months or less, or ten months or less, or nine months or less, or eight months or less, or seven months or less, or six months or less, or five months or less, or four months or less, or three months or less, or two months or less, or one month or less.

The rate of degradation, under the conditions of ASTM F1635, may be controlled through varying the nature and ratios of the components of the polyurethane. Accordingly, the polyurethane may be designed to degrade within a specific time period. This is advantageous in providing materials that are partially, fully, or substantially fully degradable in a specific time period, for example, when the functional aspects of the polyurethane are no longer required.

Melting Point

The melting point of the polyurethane of the barrier layer may be between 60° C. and 190° C. The melting point may be between 60° C. and 180° C., or between 60° C. and 170° C., or between 60° C. and 160° C., or between 60° C. and 150° C., or between 60° C. and 140° C., or between 60° C. and 130° C., or between 60° C. and 120° C., or between 60° C. and 110° C., or between 60° C. and 100° C., or between 60° C. and 100° C., or between 60° C. and 90° C., or between 60° C. and 80° C., or between 60° C. and 70° C.

Where a clear melting transition occurs the melting point may be determined by differential scanning calorimetry. Other techniques know to those skilled in the art, such as dynamic mechanical thermal analysis, may also be utilised.

Preparation of the Laminate

The barrier layer may be laminated to the foam layer by a combination of heat and pressure.

The barrier layer may be laminated to the foam layer so as there are substantially no gaps (for example, air bubbles) between the materials.

The foam layer and the barrier layer may be of substantially equal dimensions of length and width. The barrier layer may be of larger dimensions of length and/or width than the foam layer.

The barrier layer may be laminated to the foam layer through an interaction between the two materials through the application of heat or pressure or a combination of heat and pressure. Alternatively, the barrier layer may be covalently bonded to the foam layer. In an alternative and/or additional embodiment, the barrier layer may be laminated to the foam layer with the aid of a suitable adhesive according to any of the aforementioned embodiments.

The second surface of the barrier layer may be rendered substantially smooth, or substantially non-adherent to tissue by pressing against a smooth surface. For example the second surface of the barrier layer may be pressed against a PTFE surface. Preferably the pressing operation is conducted when the barrier layer polyurethane is tacky.

Accordingly, in another aspect of the present disclosure there is provided a method of preparing a tissue repair laminate comprising the steps of:
 (a) melt pressing a polyurethane resin to form a barrier layer, said barrier layer having first and second oppositely facing major surfaces;
 (b) applying a polyurethane foam layer, said foam layer having first and second oppositely facing major surfaces, to the first major surface of the barrier layer; and
 (c) fusing the foam layer and the barrier layer together through the application of heat to the second major surface of the barrier layer.

Preferably, the thickness of the barrier layer is between 0.03 and 1 mm.

Preferably, the thickness of the foam layer is between 0.2 and 5 mm.

The melt pressing may be performed at a temperature between 100 and 200° C.

The melt pressing may be performed at a pressure of up to 30 t.

The melt pressing may be performed between two smooth sheets. The sheets may be substantially smooth although some degree of surface texturing is acceptable. The melt pressing may be performed between two PTFE sheets, for example glass fibre reinforced PTFE sheets.

The fusing may be performed in the absence of applied pressure.

The fusing may be performed by applying heat to the second major surface of the barrier layer, for example by exposing the second major surface to a temperature between 100 and 200° C.

The fusing may be performed for a time between 5 seconds and minutes, preferably between 15 seconds and 90 seconds.

The barrier layer may, alternatively, be applied to the foam layer by spraying or spreading.

In other embodiments the barrier layer may be formed by other thermal processing methods known in the art such as, for example, cast extrusion and blown film extrusion.

In other embodiments the foam may be bonded or fused to the barrier layer by calendering with heat or with the use of solvents or using ultrasonic means.

Accordingly, the barrier layer may be bonded to the foam layer through ultrasonic welding. This is a particularly useful method of bonding the layers where an oriented barrier layer is utilized.

Accordingly, in another aspect of the present disclosure there is provided a method of preparing a tissue repair laminate comprising the steps of:
 (a) providing an oriented barrier layer, said barrier layer having first and second oppositely facing major surfaces;
 (b) applying a polyurethane foam layer to the first major surface of the barrier layer; and
 (c) bonding the foam layer and the barrier layer together using ultrasonic welding.

Various adhesives may be utilized to fix the barrier layer to the foam layer. The adhesive layer may be a confluent layer or discontinuous layer. Suitable adhesives include, but are not limited to, solvent-based adhesives, latex adhesives, pressure-sensitive adhesives, hot-melt adhesives, and reactive adhesives, such as a biodegradable or non-biodegradable thermoset polyurethane reactive mixture. Suitable pressure-sensitive adhesives include, but are not limited to, pressure-sensitive adhesives made from acrylics, natural latexes, styrene-butadiene rubbers, and reclaimed rubbers. Suitable hot-melt adhesives include, but are not limited to, polyamides, polyolefins, and poly(ethylene-co-vinyl acetate).

In one embodiment, the barrier layer may itself be an adhesive. In other embodiments, no adhesive may be utilised—the barrier layer is melted directly onto the foam layer.

In another aspect of the present disclosure there is provided use of a tissue repair laminate as disclosed herein for effecting tissue repair.

In another aspect of the present disclosure there is provided a method of effecting tissue repair using the tissue repair laminate as disclosed herein.

In another aspect, a method of repair of tissue damage in a subject in need thereof is provided. The method comprises surgically implanting the herein disclosed tissue repair laminate into a site of the tissue damage in the subject.

The damage may comprise, for example, a hernia, a ventral abdominal wall hernia, a rotator cuff injury, a pelvic organ prolapse, or a uro-gynecological injury. The site of the damage may be, for example, a soft tissue, a mesenchymal tissue, an intraperitoneal tissue, a rotator cuff tissue, a pelvic tissue, or a uro-gynecological tissue. The intraperitoneal tissue may be, for example, a ventral abdominal wall tissue. The rotator cuff tissue may be, for example, a rotator cuff tendon. The pelvic tissue may be, for example, a bladder tissue. The uro-gynecological tissue may be, for example, a urethral tissue. Thus, for example, the method may comprise surgically implanting the tissue repair laminate into a site, e.g. an intraperitoneal tissue, such as a ventral abdominal wall tissue, of a hernia, e.g. a ventral abdominal wall hernia, in the subject. Also for example, the method may comprise surgically implanting the tissue repair laminate, e.g. a rotator cuff repair laminate, into a site, e.g. a rotator cuff tissue, such as a rotator cuff tendon, of a rotator cuff injury in the subject. Also for example, the method may comprise surgically implanting the tissue repair laminate, e.g. a pelvic organ prolapse repair laminate, into a site, e.g. a pelvic tissue, such as a bladder tissue, of a pelvic organ prolapse in the subject. Also for example, the method may comprise surgically implanting the tissue repair laminate, e.g. a uro-gynecological reconstruction laminate, into a site, e.g. a uro-gynecological tissue, such as a urethral tissue, of a uro-gynecological injury in the subject.

The tissue repair laminates may also be useful in reinforcing tissues in surgical procedures such as abdominoplasty, breast reconstruction, midline closures, lateral closures, hernia repair, retrorectus hernia repair, Rives-Stoppa procedures, incisional hernias, cosmetic surgery, and the like.

Further features and advantages of the present disclosure will be understood by reference to the following drawings and detailed description.

DESCRIPTION OF PREFERRED EMBODIMENTS

Figure 1:
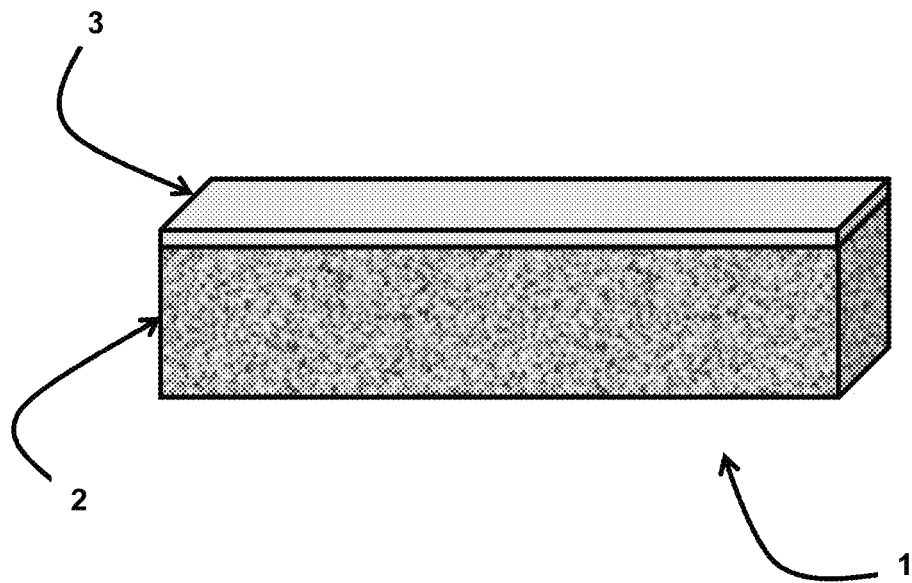
FIG. 1 is a schematic of a laminate according to one embodiment of the present disclosure.

The following is a detailed description of the disclosure provided to aid those skilled in the art in practicing the present disclosure. Those of ordinary skill in the art may make modifications and variations in the embodiments described herein without departing from the spirit or scope of the present disclosure.

Although any methods and materials similar or equivalent to those described herein can also be used in the practice or testing of the present disclosure, the preferred methods and materials are now described.

It must also be noted that, as used in the specification and the appended claims, the singular forms 'a', 'an' and 'the' include plural referents unless otherwise specified. Thus, for example, reference to 'chain extender' may include more than one chain extenders, and the like.

Throughout this specification, use of the terms 'comprises' or 'comprising' or grammatical variations thereon shall be taken to specify the presence of stated features, integers, steps or components but does not preclude the presence or addition of one or more other features, integers, steps, components or groups thereof not specifically mentioned.

Unless defined otherwise, all technical and scientific terms used herein have the meaning commonly understood by a person skilled in the art to which this disclosure belongs.

Unless specifically stated or obvious from context, as used herein, the term "about" is understood as within a range of normal tolerance in the art, for example within two standard deviations of the mean. 'About' can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein in the specification and the claim can be modified by the term 'about'.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The primary components and features used in the preparation of one or more embodiments of the tissue repair laminate as herein disclosed are discussed in detail in the following sections.

CERTAIN EMBODIMENTS

In one embodiment the present disclosure provides a tissue repair laminate wherein the polyurethane in the barrier layer is derived from:
one or more chain extenders selected from hydroxy-acetic acid 3-hydroxy-propyl ester, 6-hydroxy-hexanoic acid 2-hydroxyethyl ester, 6-hydroxy-hexanoic acid 4-hydroxybutyl ester, ethylene glycol succinic acid diester diol, ethylene glycol fumaric acid diester diol, glycolic acid-ethylene glycol dimer and lactic acid-ethylene glycol dimer;
one or more aliphatic polyester polyols; and
one or more aliphatic diisocyanates;
wherein the polyurethane of the barrier layer has a melting point between 60° C. and 190° C.; and
wherein the polyurethane of the foam layer and the barrier layer degrade, under the conditions of ASTM F1635, such that the number average molecular weight ($M_n$) of the barrier layer polyurethane and/or the mass of the foam layer independently decrease by between 10% and 90% in a period of one year or less.

In one embodiment the present disclosure provides a tissue repair laminate wherein the polyurethane in the barrier layer is derived from:
one or more chain extenders selected from hydroxy-acetic acid 3-hydroxy-propyl ester, 6-hydroxy-hexanoic acid 2-hydroxyethyl ester, 6-hydroxy-hexanoic acid 4-hydroxybutyl ester, ethylene glycol succinic acid diester diol, ethylene glycol fumaric acid diester diol, glycolic acid-ethylene glycol dimer and lactic acid-ethylene glycol dimer;
one or more aliphatic polyester polyols; and
one or more aliphatic diisocyanates selected from 4,4'-methylene dicylcohexyl diisocyanate (HMDI), 1,6-hexane diisocyanate (HDI), 1,4-butane diisocyanate (BDI), L-lysine diisocyanate (LDI), 2,4,4-trimethylhexamethylenediisocyanate;
wherein the polyurethane of the barrier layer has a melting point between 60° C. and 190° C.; and wherein the polyurethane of the foam layer and the barrier layer degrade, under the conditions of ASTM F1635, such that the number average molecular weight ($M_n$) of the barrier layer polyurethane and/or the mass of the foam layer independently decrease by between 10% and 90% in a period of one year or less.

In one embodiment the present disclosure provides a tissue repair laminate wherein the polyurethane in the barrier layer is derived from:
one or more chain extenders selected from hydroxy-acetic acid 3-hydroxy-propyl ester, 6-hydroxy-hexanoic acid 2-hydroxyethyl ester, 6-hydroxy-hexanoic acid 4-hydroxybutyl ester, ethylene glycol succinic acid diester diol, ethylene glycol fumaric acid diester diol, glycolic acid-ethylene glycol dimer and lactic acid-ethylene glycol dimer;
one or more aliphatic polyester polyols derived from one or more diol initiators and at least one hydroxy acid and/or cyclic ester; and
one or more aliphatic diisocyanates selected from 4,4'-methylene dicylcohexyl diisocyanate (HMDI), 1,6-hexane diisocyanate (HDI), 1,4-butane diisocyanate (BDI), L-lysine diisocyanate (LDI), 2,4,4-trimethylhexamethylenediisocyanate;
wherein the polyurethane of the barrier layer has a melting point between 60° C. and 190° C.; and
wherein the polyurethane of the foam layer and the barrier layer degrade, under the conditions of ASTM F1635, such that the number average molecular weight ($M_n$) of the barrier layer polyurethane and/or the mass of the foam layer independently decrease by between 10% and 90% in a period of one year or less.

In one embodiment the present disclosure provides a tissue repair laminate wherein the polyurethane in the barrier layer is derived from:
one or more chain extenders selected from hydroxy-acetic acid 3-hydroxy-propyl ester, 6-hydroxy-hexanoic acid 2-hydroxyethyl ester, 6-hydroxy-hexanoic acid 4-hydroxybutyl ester, ethylene glycol succinic acid diester diol, ethylene glycol fumaric acid diester diol, glycolic acid-ethylene glycol dimer and lactic acid-ethylene glycol dimer;
one or more aliphatic polyester polyols derived from one or more diol initiators and at least one hydroxy acid, diacid or cyclic ester, or combinations thereof, wherein the one or more diol initiators is selected from ethylene glycol, 1,3-propanediol, 1,2-propanediol, 1,4-butanediol, pentanediol, hexamethylenediol, heptanediol, nonanediol, dodecanediol, 2-ethyl-1,3-hexanediol (EHD), 2,2,4-trimethyl pentane-1,3-diol (TMPD), 1,6-hexanediol, 1,4-cyclohexane dimethanol, diethylene glycol, dipropylene glycol, and combinations thereof and wherein the at least one hydroxy acid is selected from 1-lactic acid, d-lactic acid, d,l-lactic acid, mandelic acid, phenyl-lactic acid, valeric acid or glycolic acid; wherein the one or more diacids is selected from oxalic acid, malonic acid, succinic acid, glutaric acid, adipic acid, pimelic acid, suberic acid, azelaic acid, sebacic acid, undecanedioic acid, dodecanedioic acid, tridecanedioic acid, and hexadecanedioic acid and wherein the cyclic ester is selected from ε-caprolactone, glycolide, lactide, mandelide, and p-dioxanone; and
one or more aliphatic diisocyanates selected from 4,4'-methylene dicylcohexyl diisocyanate (HMDI), 1,6-hexane diisocyanate (HDI), 1,4-butane diisocyanate (BDI), L-lysine diisocyanate (LDI), 2,4,4-trimethylhexamethylenediisocyanate;
wherein the polyurethane of the barrier layer has a melting point between 60° C. and 190° C.; and wherein the polyurethane of the foam layer and the barrier layer degrade, under the conditions of ASTM F1635, such that the number average molecular weight ($M_n$) of the barrier layer polyurethane and/or the mass of the foam layer independently decrease by between 10% and 90% in a period of one year or less.

In one embodiment the present disclosure provides a tissue repair laminate comprising:
(a) a biodegradable polyurethane foam layer having first and second oppositely facing major surfaces; and
(b) a polyurethane barrier layer having first and second oppositely facing major surfaces;
wherein the first major surface of said barrier layer and the second major surface of said foam layer face each other;
wherein said foam layer comprises a pore structure configured for cellular infiltration;
wherein the average pore size of said foam layer is greater than 75 μm; and
wherein the second major surface of said barrier layer is less adherent to tissue than the first major surface of said foam layer.

In one embodiment the present disclosure provides a tissue repair laminate comprising:
(a) a biodegradable polyurethane foam layer having first and second oppositely facing major surfaces; and
(b) a polyurethane barrier layer having first and second oppositely facing major surfaces;
wherein the first major surface of said barrier layer and the second major surface of said foam layer face each other;
wherein said foam layer comprises a pore structure configured for cellular infiltration;
wherein the average pore size of said foam layer is greater than 100 μm; and
wherein the second major surface of said barrier layer is less adherent to tissue than the first major surface of said foam layer.

In one embodiment the present disclosure provides a tissue repair laminate comprising:
(a) a biodegradable polyurethane foam layer having first and second oppositely facing major surfaces; and
(b) a biodegradable polyurethane barrier layer having first and second oppositely facing major surfaces;
wherein the first major surface of said barrier layer and the second major surface of said foam layer face each other;
wherein said foam layer comprises a pore structure configured for cellular infiltration;
wherein the average pore size of said foam layer is greater than 75 μm; and
wherein the second major surface of said barrier layer is less adherent to tissue than the first major surface of said foam layer.

In one embodiment the present disclosure provides a tissue repair laminate comprising:
(a) a biodegradable polyurethane foam layer having first and second oppositely facing major surfaces; and
(b) a biodegradable polyurethane barrier layer having first and second oppositely facing major surfaces;
wherein the first major surface of said barrier layer and the second major surface of said foam layer face each other;
wherein said foam layer comprises a pore structure configured for cellular infiltration;
wherein the average pore size of said foam layer is greater than 100 μm; and
wherein the second major surface of said barrier layer is less adherent to tissue than the first major surface of said foam layer.

Bioactive Substances

Bioactive substances may optionally be added to the polyurethanes of the foam layer, the barrier layer or both layers.

The bioactive substance may be formulated with the polyurethane to form a composition. The formulation may be facilitated by, for example, melt processing, additive manufacturing or dissolution in an appropriate solvent.

Bioactive substances may be synthetic molecules, biomolecules, or multimolecular entities and include, but are not limited to, enzymes, organic catalysts, ribozymes, organometallics, proteins, glycoproteins, peptides, polyamino acids, antibodies, nucleic acids, steroidal molecules, antibiotics, silver, silver oxide, antivirals, antimycotics, anticancer agents, analgesic agents, antirejection agents, immunosuppressants, cytokines, carbohydrates, oleophobics, lipids, extracellular matrix and/or its individual components, demineralized bone matrix, hydroxyapatite, tricalcium phosphate, pharmaceuticals, chemotherapeutics, and therapeutics. Cells and non-cellular biological entities, such as viruses, virus vectors and prions can also be bioactive substances. The bioactive substances may be chemically bonded to the polyurethane.

The biological effect in humans or animals is for medical, therapeutic, cosmetic and veterinary purposes, and encompasses pharmaceuticals including drugs, cosmeceuticals, nutraceuticals, and nutritional agents. It will be appreciated that some of bioactive compounds can be classified in more than one of these classes.

A wide range of bioactive substances may be incorporated into the presently disclosed polyurethanes and may be consequently delivered with the tissue repair laminates as herein disclosed.

Examples include, but are not limited to, cardiovascular drugs, in particular antihypertensive agents (e.g. calcium channel blockers or calcium antagonists) and antiarrhythmic agents; congestive heart-failure pharmaceuticals; inotropic agents; vasodilators; ACE inhibitors; diuretics; carbonic anhydrase inhibitors; cardiac glycosides; phosphodiesterase inhibitors; α-blockers; β-blockers; sodium channel blockers; potassium channel blockers; β-adrenergic agonists; platelet inhibitors; angiotensin antagonists; anticoagulants; thrombolytic agents; treatments for bleeding; treatments for anaemia; thrombin inhibitors; antiparasitic agents; antibacterial agents; insulin; human growth hormone and peptides; vaccines; anti-inflammatory agents, in particular non-steroidal anti-inflammatory agents (NSAIDs), more particularly COX-2 inhibitors; steroidal anti-inflammatory agents; prophylactic anti-inflammatory agents; anti glaucoma agents; mast cell stabilisers; mydriatics; agents affecting the respiratory system; allergic rhinitis pharmaceuticals; a adrenergic agonists; corticosteroids; chronic obstructive pulmonary disease pharmaceuticals; xanthine-oxidase inhibitors; anti-arthritis agents; gout treatments; autacoids and autacoid antagonists; anti mycobacterial agents; antifungal agents; antiprotozoal agents; anthelmintic agents; antiviral agents especially for respiratory, herpes, cyto-megalovirus, human immunodeficiency virus and hepatitis infections; treatments for leukaemia and Kaposi's sarcoma; pain management agents in particular opioids, anaesthetics and analgesics; neuroleptics; sympathomimetic pharmaceuticals; adrenergic agonists; drugs affecting neurotransmitter uptake or release; anticholinergic pharmaceuticals; anti haemorrhoid treatments; agents to prevent or treat radiation or chemotherapeutic effects; lipogenesis drugs; fat reducing treatments; anti-obesity peptides; antiobesity agents such as lipase inhibitors; sympathomimetic agents; treatments for gastric ulcers and inflammation such as proton pump inhibitors; prostaglandins; VEGF inhibitors; antihyperlipidemic agents, in particular statins; drugs that affect the central nervous system (CNS) such as antipsychotic, antiepileptic and anti-seizure drugs (anticonvulsants), psychoactive drugs, stimulants, antianxiety and hypnotic drugs, antidepressant drugs; anti Parkinson's pharmaceuticals; hormones and fragments thereof such as sex hormones; growth hormone antagonists; gonadotropin releasing hormones and analogues thereof; steroid hormones and their antagonists; selective estrogen modulators; growth factors; anti diabetic pharmaceuticals such as insulin, insulin fragments, insulin analogues, glucagon like peptides and hypoglycaemic agents; H1, H2, H3 and H4 antihistamines; peptide, protein, polypeptide, nucleic acids and oligonucleotide pharmaceuticals; analogues, fragments and variants of natural proteins, polypeptides, oligonucleotides and nucleic acids and such like compounds; agents used to treat migraine headaches; asthma pharmaceuticals; cholinergic antagonists; glucocorticoids; androgens; antiandrogens; inhibitors of adrenocorticoid biosynthesis; osteoporosis treatments such as biphosphonates; antithyroid pharmaceuticals; cytokine agonists; cytokine antagonists; anticancer drugs; antialzheimer drugs; HMG-CoA reductase inhibitors; fibrates; cholesterol absorption inhibitors; HDL cholesterol elevating agents; triglyceride reducing agents; anti-ageing or anti-wrinkle agents; precursor molecules for the generation of hormones; proteins such as collagen and elastin; antibacterial agents; anti acne agents; antioxidants; hair treatments and skin whitening agents; sunscreens, sun protectants and filters; variants of human apolipoprotein; precursor molecules for generation of hormones; proteins and peptides thereof; amino acids; plant extracts such as grape seed extract; DHEA; isoflavones; nutritional agents including vitamins, phytosterols and iridoid gylcosides, sesquiterpene lactones, terpenes, phenolic glycosides, triterpenes, hydroquinone derivatives, phenylalkanones; antioxidants such as retinol and other retinoids including retinoic acid and co enzyme Q10; omega-3-fatty acids; glucosamine; nucleic acids, oligonucleotides, antisense pharmaceuticals; enzymes; cytokines; cytokine analogues; cytokine agonists; cytokine antagonists; immunoglobulins; antibodies; antibody pharmaceuticals; gene therapies; lipoproteins; erythropoietin; vaccines; small and large molecule therapeutic agents for the treatment, or prevention of human and animal diseases such as allergy/asthma, arthritis, cancer, diabetes, growth impairment, cardiovascular diseases, inflammation, immunological disorders, baldness, pain, ophthalmological diseases, epilepsy, gynaecological disorders, CNS diseases, viral infections, bacterial infections, parasitic infections, GI diseases, obesity, and haemological diseases.

It is to be understood that pharmaceutically, nutraceutically or cosmeceutically acceptable derivatives of bioactive substances are included within the scope of the present disclosure.

The term "pharmaceutically, nutraceutically or cosmeceutically acceptable derivatives" includes, but is not limited to, pharmaceutically, nutraceutically or cosmeceutically acceptable salts, esters, salts of such esters, ethers, or any other derivative including prodrugs and metabolites, which upon administration to a subject (e.g. patient, human or animal) in need is capable of providing, directly or indirectly, a bioactive substance as otherwise described herein.

As used herein, the term "pharmaceutically, nutraceutically or cosmeceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio.

Pharmaceutically, nutraceutically or cosmeceutically acceptable salts are well known in the art. For example, S. M. Berge, et al. describe pharmaceutically, nutraceutically or cosmeceutically acceptable salts in detail in J. Pharmaceutical Sciences, 66:1-19, 1977.

Examples of pharmaceutically, nutraceutically or cosmeceutically acceptable nontoxic acid addition salts are salts of an amino group formed with inorganic acids such as hydrochloric acid, hydrobromic acid, phosphoric acid, sulfuric acid and perchloric acid or with organic acids such as— acetic-acid, oxalic acid, maleic acid, tartaric acid citric acid, succinic acid, or malonic acid or by using other methods used in the art such as ion exchange.

Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2 hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

The term "pharmaceutically, nutraceutically or cosmeceutically acceptable ester" refers to esters which are hydrolysed in vivo and include those that break down readily in the human body to leave the parent compound or a salt thereof. Suitable ester groups include, for example, those derived from pharmaceutically, nutraceutically or cosmeceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of esters include formates, acetates, propionates, butyrates, acrylates and ethylsuccinates.

The term "pharmaceutically, nutraceutically or cosmeceutically acceptable prodrugs" as used herein includes those prodrugs of the biologically active substances which are, within the scope of sound medical judgment, suitable for use in contact with the tissues of a subject with undue toxicity, irritation, allergic response, and the like, commensurate with a reasonable benefit/risk ratio, and effective for their intended use, as well as the zwitterionic forms, where possible, of the biologically active substances.

The term "prodrug" refers to compounds that are rapidly transformed in vivo to yield a parent compound, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987.

The present disclosure is further not limited solely to the administration of one biologically active substance: more than one biologically active substance or other therapeutic compounds may be incorporated into the foam layer and/or barrier layer.

Degradation

The polyurethanes of either the foam layer or the barrier layer or both layers of the tissue repair laminate of the present disclosure may be designed to degrade in vivo or under in vivo conditions at controlled rates. The polyurethanes may be degradable at temperatures between 35 and 42° C.

In some embodiments the number average molecular weight ($M_n$) of the barrier layer polyurethane and the mass of the foam layer may independently decrease by between 20% and 90% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the barrier layer polyurethane and the mass of the foam layer may independently decrease by between 30% and 90% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the barrier layer polyurethane and the mass of the foam layer may independently decrease by between 40% and 90% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the barrier layer polyurethane and the mass of the foam layer may independently decrease by between 50% and 90% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the barrier layer polyurethane and the mass of the foam layer may independently decrease by between 60% and 90% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the barrier layer polyurethane and the mass of the foam layer may independently decrease by between 70% and 90% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the barrier layer polyurethane and the mass of the foam layer may independently decrease by between 80% and 90% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the barrier layer polyurethane and the mass of the foam layer may independently decrease by between 20% and 70% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the barrier layer polyurethane and the mass of the foam layer may independently decrease by between 30% and 70% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the barrier layer polyurethanes and the mass of the foam layer may independently decrease by between 40% and 70% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the barrier layer polyurethane and the mass of the foam layer may independently decrease by between 50% and 70% in a period of eleven months or less, or ten months or less, or nine months or less, or eight months or less, or seven months or less, or six months or less, or five months or less, or four months or less, or three months or less, or two months or less, or one month or less.

n some embodiments the number average molecular weight ($M_n$) of the barrier layer polyurethanes and the mass of the foam layer may independently decrease by between 60% and 70% in a period of eleven months or less, or ten months or less, or nine months or less, or eight months or less, or seven months or less, or six months or less, or five months or less, or four months or less, or three months or less, or two months or less, or one month or less.

FIG. 1 illustrates a tissue repair laminate (1) according to an embodiment of the present disclosure comprising foam layer (2) and barrier layer (3).

Figure 2:
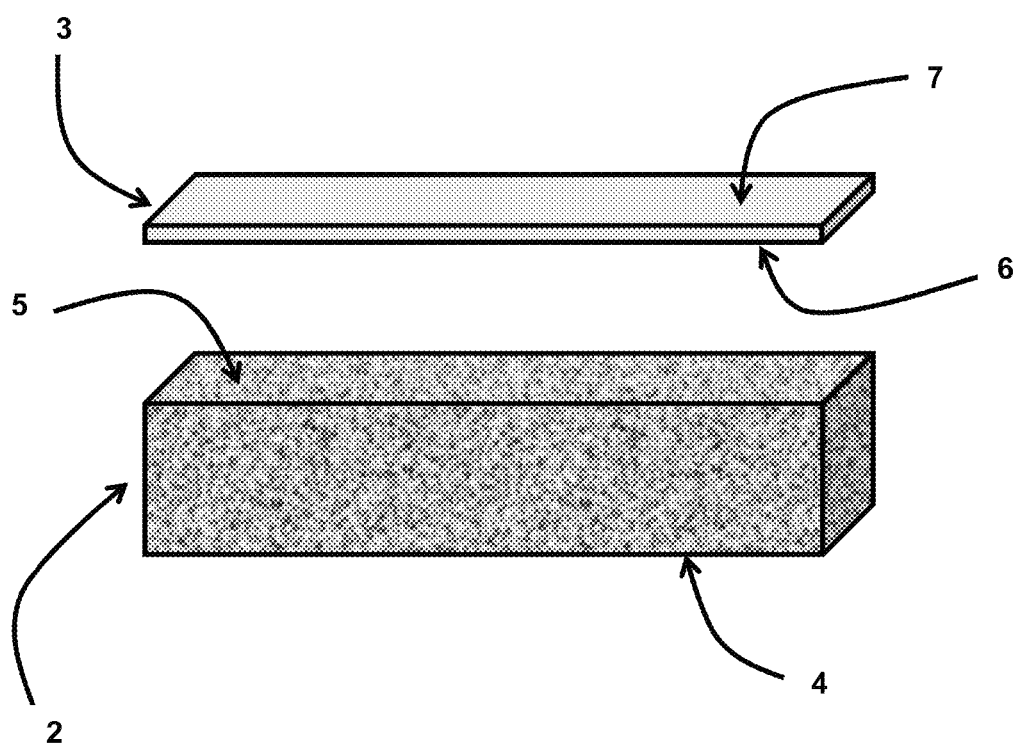
FIG. 2 is an exploded view of a laminate according to one embodiment of the present disclosure.

FIG. 2 illustrates an exploded view of the tissue repair laminate of FIG. 1 comprising foam layer (2) and barrier layer (3). The foam layer comprises first (4) and second (5) major surfaces and the barrier layer comprises first (6) and second (7) major surfaces.

Figure 3:
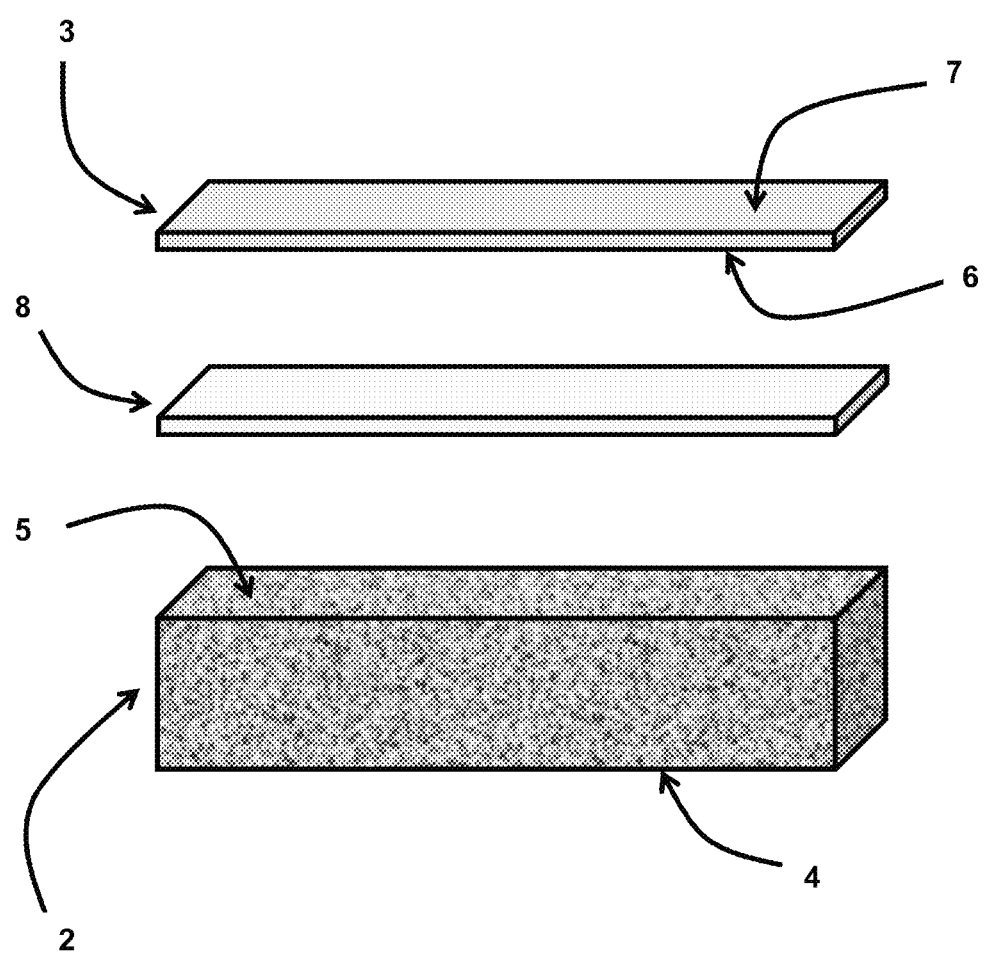
FIG. 3 is an exploded view of a laminate according to one embodiment of the present disclosure.

FIG. 3 illustrates an exploded view of a tissue repair laminate according to another embodiment of the present disclosure comprising foam layer (2), barrier layer (3) and intermediate adhesive layer (8). The foam layer comprises first (4) and second (5) major surfaces and the barrier layer comprises first (6) and second (7) major surfaces.

The following Examples describe the preparation and use of the tissue repair laminates according to the present disclosure and are intended to illustrate the disclosure. The Examples are not to be construed as limiting in any way the scope of the present disclosure.

EXAMPLES

Foam Layer Preparation

A biodegradable polyurethane thermoset foam was prepared according to the present disclosure. The foam was cut into sheets of various thickness using conventional foam slicing equipment.

Barrier Layer Preparation

Example 1: Polyol Synthesis

Polyols were prepared by condensation of L-lactic acid (LLA), ε-caprolactone (CL) and 1,4-butane diol (BDO). All components were weighed into a glass reactor fitted with stirring, nitrogen outgassing, a condenser, and a heat source. The temperature was set to between 130° C. and 210° C. and the stirring and nitrogen flow started. Water was removed from the vessel via the condenser as the reaction proceeded. The reaction was continued until completion as indicated by residual acid measurement at which point the polyol was cooled and stored for use.

Polyols of molecular weight of about 400 were prepared as above using weight ratios of LLA:CL of 30:70 along with BDO initiator.

In a specific example, 3887 g of 1,4-butane diol (BDO), 3953 g of 90% lactic acid, and 10520 g of ε-caprolactone were added to a reactor fitted with stirring, condenser and a nitrogen atmosphere. The mixture was heated at 200° C. and heating was removed once the acid number was 1.9 mg KOH/g.

Example 2: Chain Extender Synthesis

The chain extender was prepared by ring opening polymerisation of ε-caprolactone (CL) and 1,4-butane diol (BDO) in a 1:5 molar ratio. The temperature was set to between 130° C. and 210° C. with stirring and nitrogen. The reaction was continued until completion as indicated by gas chromatography (GC) analysis at which point the chain extender was cooled and stored for use.

In an example, 706.5 g ε-caprolactone and 2792.5 g BDO were added to a reactor fitted with heating and stirring. The mixture was heated at 200° C. until ε-caprolactone was no longer detectable by GC. GC testing of the product indicated 67.9% BDO, 26.7% dimer and 3.8% trimer.

Example 3: Prepolymer Synthesis 6000.5 g of the above prepared polyol was charged to a reactor fitted with stirring and nitrogen and 3467.5 g 1,6-hexane diisocyanate (HDI) added. The mixture was heated to 60° C. and the reaction exotherm reached 90° C. The mixture was then cooled to 60° C. and 128.27 g of the above prepared chain extender and 0.2 g catalyst added. The exotherm reached 82° C. The NCO content of the prepolymer was found to be 7.607%.

Example 4: Polymer Synthesis 9458.5 g of the above prepared prepolymer was weighed into a 20 litre container, and 771.5 g dry BDO added along with 0.7 g zinc based catalyst. The mixture was stirred and then poured into PTFE-lined trays and cured in an oven for a period of 2 hours at 120° C. The polymer was then granulated using a Zerma GSL 180/300 granulator.

Example 5: Polymer Synthesis (42% Hard Segment)

Under nitrogen and stirring, 3 kg of the polyol of Example 1 was combined with HDI (1.734 kg). BDO-CL (Example 2; 63.5 g) and organozinc catalyst were added with heating to complete a prepolymer and the isocyanate content assayed. This was then chain extended using BDO (407.6 g) and further zinc catalyst. The stirred mixture was then poured into PTFE-lined trays and cured in an oven for 2 hours at 120° C. The cured polymer was then granulated.

Example 6: Cast Film for Barrier Layer

Dried granulated polymer from Example 5 was extruded on a small-scale cast film line equipped with extruder and chill rolls to provide a continuous film of between 235 and 420 μm thickness. Temperature during extrusion was between 160-185° C., and a lower temperature in the feeding zone.

Example 7: Stretching—Machine Direction Orientation (MDO)

Cast film from Example 6 (300 μm thickness) was run through a continuous stretching machine (MDO) and stretched with heat (from 40° C. to 90° C.). Stretch ratios of up to 1:5.5 were used and the measured residual stretching ratios were between 1:2.3 and 1:4. The stretching was conducted in two manners—using a roll of prepared film, and also in series with the immediate output of the cast film line being fed into the continuous stretcher as a continuous process. The film was collected on separate rolls for each condition.

Example 8: Melt Pressed Barrier Layer

Polymer granules prepared as in Example 4 were melt pressed between glass fibre-reinforced PTFE sheets at 175° C., 10 t pressure on a Carver melt-press, to form a film 0.2 mm thick.

Example 9: Laminate Preparation

A 1 mm foam sheet (biodegradable polyester-urethane-urea thermoset foam) was applied to the top of the melt-pressed barrier layer of Example 8 and heated on the melt-press platen without pressure at 175° C. for 45 seconds to bond the two layers together. Specimens of the laminate were cut (3 cm×7 cm) and heat sealed individually in two layers of medical grade packaging (oriented polyamide and foil pouches). Sterilised at >25 kGy gamma irradiation.

The properties of the laminate were measured on an Instron 5566 mechanical testing machine under both dry and wet conditions after incubation at 37° C. overnight and the results collected in Table 1.

TABLE 1

| Material | Suture retention (N) | UTS (machine direction) (N/cm) | Ball burst strength (N/cm) | Tear resistance (N) |
| --- | --- | --- | --- | --- |
| Laminate (Dry) | 41.3 | 52.4 | 173 | 21.4 |
| Laminate (Wet) | 39.5 | 46.2 | 84 | 22.5 |

Example 10: Spunbond

A spunbond polyurethane was prepared using the same polyurethane as for the above prepared barrier layer.

Six batches of polyurethane were prepared and granulated utilising the method outlined above and 7 kg of each batch blended together for a total of 41 kg. The material was extruded and calendered on a 1 m spunbond line.

The areal weight (weight of fabric per unit area) of the spunbond fabric (dry) was measured as 198 g/m².

Specimens were cut for mechanical testing on an Instron 5566 mechanical testing machine. The specimens were incubated in distilled water at 37° C. overnight prior to testing. Table 2 collects the results of testing.

TABLE 2

| Test | Result | Units |
| --- | --- | --- |
| Ball burst strength | 97 ± 19 | N/cm |
| Tear resistance (machine direction) | 10.6 ± 1.8 | N |
| Tear resistance (transverse direction) | 11.8 ± 1.1 | N |
| Suture retention (machine direction) | 17.7 ± 3.3 | N |
| Suture retention (transverse direction) | 21.5 ± 2.3 | N |
| UTS (machine direction) | 24.4 ± 2.0 | N/cm |
| UTS (transverse direction) | 19.0 ± 1.8 | N/cm |

Example 11: Warp Knit

A warp knit polyurethane was prepared using the same polyurethane as for the above prepared barrier layer and spunbond.

The polyurethane was extruded on a conventional extruder equipped with a take-off system including heated godets. Spools of monofilament were produced and tested and the results are collected in Table 3.

TABLE 3

| Diameter (mm) | Linear Density (Denier) | Break Load (N) | Max. Elongation (%) | Tenacity (gf/denier) | Peak Stress (MPa) |
| --- | --- | --- | --- | --- | --- |
| 0.24 | 453 | 3.45 ± 0.19 | 151 ± 15 | 0.78 ± 0.04 | 75 ± 7 |
| 0.23 | 440 | 3.23 ± 0.15 | 102 ± 12 | 0.75 ± 0.03 | 86 ± 9 |
| 0.23 | 441 | 3.59 ± 0.24 | 119 ± 17 | 0.83 ± 0.06 | 79 ± 4 |
| 0.23 | 454 | 3.98 ± 0.12 | 158 ± 5 | 0.90 ± 0.03 | 154 ± 25 |
| 0.23 | 452 | 3.58 ± 0.33 | 141 ± 23 | 0.81 ± 0.08 | 94 ± 13 |
| 0.25 | 453 | 3.33 ± 0.12 | 138 ± 13 | 0.75 ± 0.03 | 66 ± 3 |
| 0.23 | 449 | 3.56 ± 0.14 | 144 ± 13 | 0.81 ± 0.03 | 126 ± 12 |
| 0.23 | 452 | 3.46 ± 0.11 | 108 ± 14 | 0.78 ± 0.03 | 125 ± 15 |
| 0.22 | 425 | 3.44 ± 0.06 | 170 ± 1 | 0.83 ± 0.01 | 99 ± 9 |
| 0.22 | 400 | 3.43 ± 0.32 | 156 ± 21 | 0.87 ± 0.08 | 83 ± 6 |
| 0.22 | 399 | 3.43 ± 0.32 | 156 ± 21 | 0.87 ± 0.08 | 83 ± 6 |

The spools of filament were warp-knitted using a double-knit pattern to produce a mesh which was then stentered. The mesh had an issue with curling that was not fixed under the conditions of the stentering. Samples of mesh were hydrated in water for 2 hours prior to mechanical testing the results of which are collected in Table 4.

TABLE 4

| Evaluation | Result | Units |
| --- | --- | --- |
| Pore size | 0.602 ± 0.034 | mm |
| Tensile strength (transverse direction) | 32.4 ± 2.48 | N/cm |
| Tensile strength (machine direction) | 28.39 ± 5.88 | N/cm |
| Suture retention (transverse direction) | 16.28 ± 0.93 | N |
| Suture retention (machine direction) | 18.37 ± 4.06 | N |
| Areal weight | 336.28 ± 4.25 | g/m² |
| Thickness | 0.939 ± 0.025 | mm |
| Ball burst strength | 94.88 ± 1.49 | N/cm |

Example 12: Ultrasonic Welding

Figure 7:
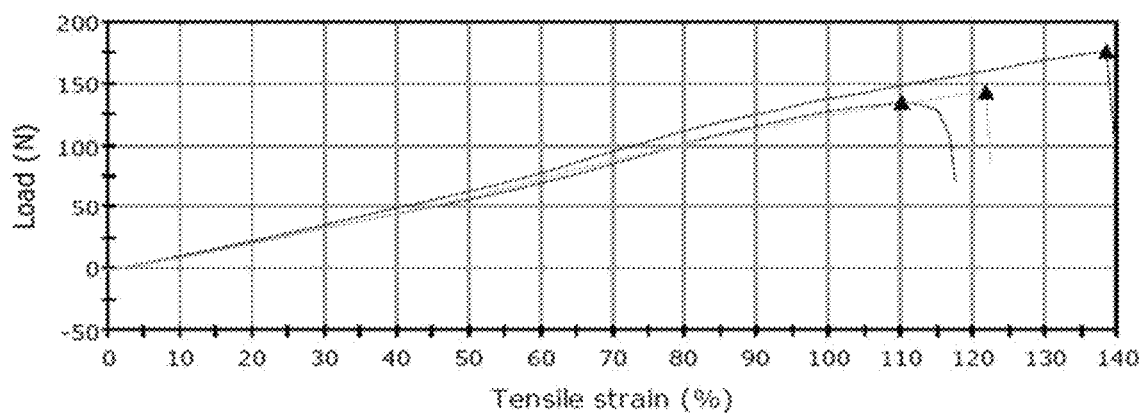
FIG. 7 illustrates the stress strain curve for a laminate according to one embodiment of the present disclosure.

A laminate was prepared using film of example 7 and annealed at 70° C. prior to use, and 2 mm thick foam (biodegradable polyester-urethane-urea thermoset foam). The foam sheet was placed on top of the stretched and annealed film and welded together using an ultrasonic probe (40 kHz probe, Dukane IQ) with settings of 3 Joules per weld and 50 Amplitude. The sheets were welded with a 4 mm spot weld and in a square array of 14 mm spacing (centre to centre). Tensile specimens were prepared and tested on an Instron model 5566 (10 cm length, 2.6 cm width, 2 columns of welds per specimen, 50 mm gauge length, 500 mm/min). The welds were secure and the film was smooth on the non-bonded side. The average mechanical properties of the laminate was as follows: Ultimate tensile strength 56.6 N/cm, Elongation 126%. FIG. 7 illustrates the stress-strain curve for the laminate.

Comparative Example 1: Mechanical Test Results

Mechanical tests were performed on foam layers absent the presence of the barrier layer. The tests were performed on foam layers of 2 mm, 3 mm and 4 mm thickness, both wet and dry, and at high and low strain rates. Table 5 collects the results of Ball Burst Strength and Suture Retention.

TABLE 5

| Thickness and Condition | Ball burst strength (N/cm) | Suture retention (N) |
| --- | --- | --- |
| 2 mm, 300 mm/min, wet | 7 | 0.65 |
| 2 mm, 300 mm/min, dry | 21 | 1.43 |
| 3 mm, 300 mm/min, wet | 10 | 0.89 |
| 3 mm, 300 mm/min, dry | 28 | 2.14 |
| 4 mm, 300 mm/min, wet | 11 | 1.19 |
| 4 mm, 300 mm/min, dry | 36 | 2.35 |

Compared to the Ball Burst Strengths and Suture Retention Strengths of the laminates in Table 1, the foam layers absent a barrier layer performed very poorly. Even foam layers of 4 mm thickness performed extremely poorly compared to the 1 mm foam layer laminated with a 200 μm barrier layer.

In-Vivo Testing

Twenty five 3-month old male New Zealand white rabbits were randomly assigned to five groups of five each. Five separate test articles were implanted to repair the abdominal wall defects and included Prolene® (Ethicon), a monofilament non-biodegradable polypropylene mesh, three configurations of a polyurethane article (Test samples A, B, and C), and AlloDerm® (Life Cell Corporation) a dermal-derived extra cellular matrix. The groups were: Group 1 Test A; Group 2 Test B; Group 3 Test C; Group 4 AlloDerm®; and Group 5 Prolene®.

Test A was a laminate according to the present disclosure. Comparative Test B was the spunbond polyurethane mesh and Comparative Test C was the knitted polyurethane mesh. Each of the test articles were 7 cm×3 cm in size (surface area 21 cm$^2$).

On Study Day 1 a veterinary surgeon created a full thickness, 7×3 cm abdominal wall defect in each rabbit, and repaired the defect with the above described synthetic and biologic materials. Test A (the laminate of the present disclosure) was used such that the foam layer faced the abdominal wall and the barrier layer faced the internal organs.

Two weeks postoperatively (Day 14), the animals were sacrificed, and the extent and severity of adhesion formation was assessed. The size and integrity of the grafts in the five experimental groups were analyzed and compared. The animals were carefully evaluated for the presence and the degree of intra-abdominal adhesions and measurement of graft size to check for contraction, if any. Biopsies were taken from within 1 cm from the suture line as well as from the centre of the graft and fixed for histopathology to include: quantification of vascular elements; cellularity; collagen content; and inflammation. All sections were stained with hematoxylin and eosin (H & E). In relation to adhesions the scales in Tables 6 and 7 were employed.

TABLE 6

| Score of Adhesions Amount | % of device area in adhesions |
| --- | --- |
| 0 | No adhesions |
| 1 | ≤25 |
| 2 | ≤50 |
| 3 | ≤75 |
| 4 | >75 |

TABLE 7

| Score of Type of Adhesions | Definition |
| --- | --- |
| 0 | NONE- absence of adhesions |
| 1 | MILD- thin adhesions with easy release |
| 2 | MODERATE- adhesions that need blunt dissection to be released |
| 3 | Firm adhesions in which only significant strength is able to release, injuring partially or totally the involved gut |

The following summarizes the tissue reactions observed with respect to the devices employed.

Group 1 (test A): Adhesion Scores (percent of area adhered) for animals 1001, 1002, 1003, 1004, and 1005 were 0, 0, 0.5, 0.5, and 0.5 respectively (Ave=0.3); Type of adhesion scores were 0, 0, 0.5, 1, and 0.5 respectively (Ave=0.4); No abscess. The only reason for the adhesion scores above zero were small adhesions to the suture line—not to the article itself.

Group 2 (test B): Adhesion Scores (percent of area adhered) for animals 2001, 2002, 2003, 2004, and 2005 were 4, 4, 2, 4, and 1 respectively (Ave=3.0); Type of adhesion scores were 3, 3, 3, 3, and 3 respectively (Ave=3.0); No abscess.

Group 3 (test C): Adhesion Scores (percent of area adhered) for animals 3001, 3002, 3003, 3004, and 3005 were 2, 4, 3, 4, and 4 respectively (Ave 3.4); Type of adhesion scores were 2, 3, 3, 3, and 3 respectively (Ave=2.8); No abscess.

Group 4 (AlloDerm®): Adhesion Scores (percent of area adhered) for animals 4001, 4002, 4003, 4004, and 4005 were 1, 1, 0, 0, and 0 respectively (Ave=0.4); Type of adhesion scores were 1, 2, 0, 0, and 0 respectively (Ave=0.6); No abscess. The only reason for the adhesion scores above zero were small adhesions to the suture line—not to the article itself.

Group 5 (Prolene®): Adhesion Scores (percent of area adhered) for animals 5001, 5002, 5003, 5004, and 5005 were 4, 4, 4, 4, and 4 respectively (Ave 4.0); Type of adhesion scores were 3, 3, 3, 3, and 3 respectively (Ave=3.0); No abscess; most or all of the surface of the article was adhered to the large intestine.

Figure 4:
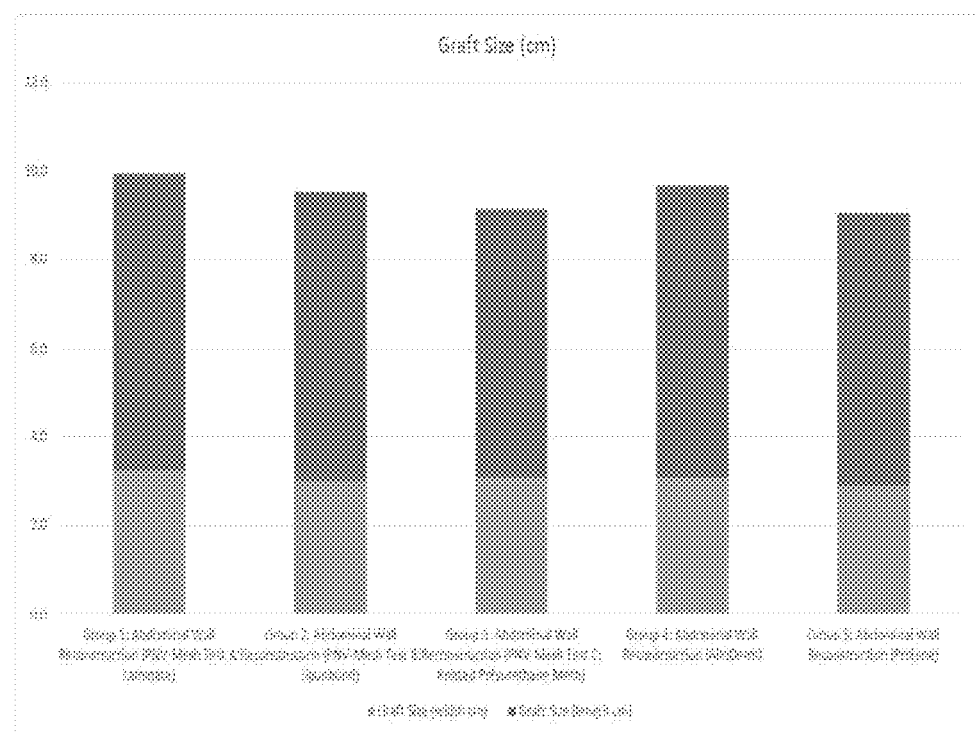
FIG. 4 is a bar chart illustrating results of graft size after 14 days in vivo.
Figure 5:
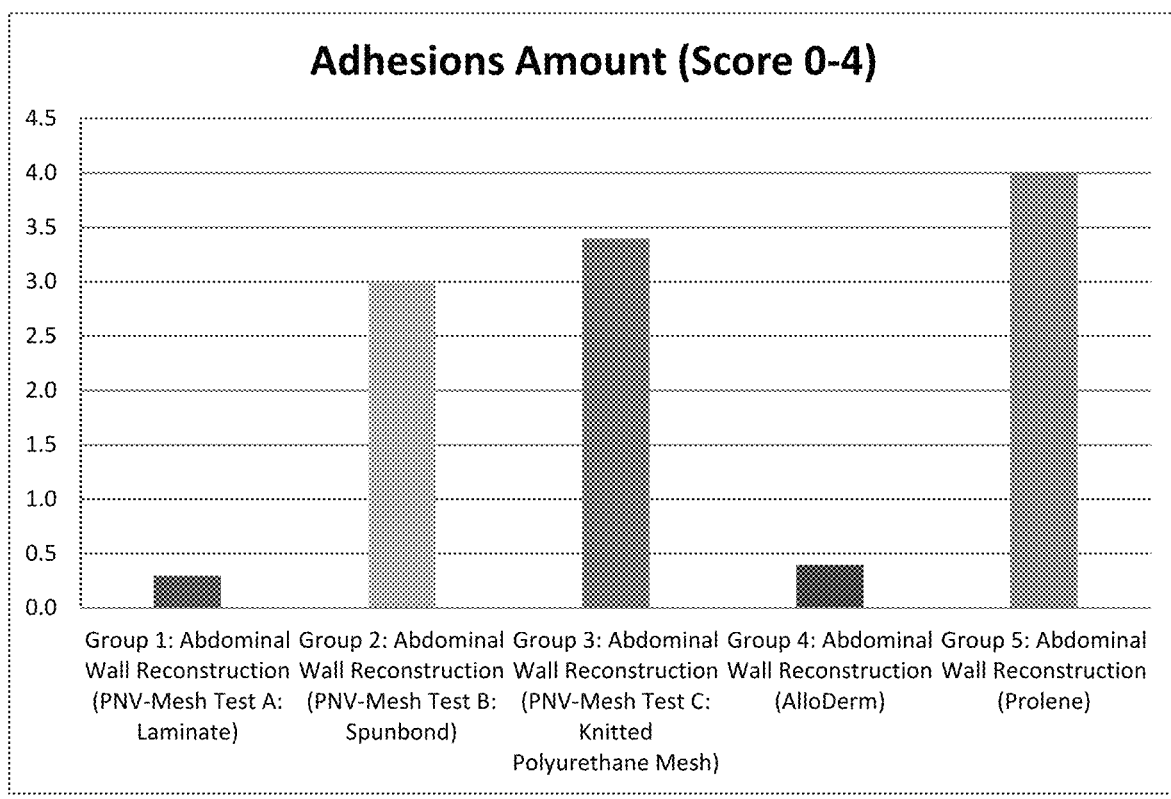
FIG. 5 is a bar chart illustrating results of adhesion amount.

Tables 8 and 9 collect the average results on adhesion and FIGS. 4 and 5 illustrate the results graphically.

TABLE 8

| Group | Adhesions amounts (Score 0-4) |
|---|---|
| 1 | 0.3 |
| 2 | 3.0 |
| 3 | 3.4 |
| 4 | 0.4 |
| 5 | 4.0 |

TABLE 9

| Group | Type of adhesions (Score 0-3) |
|---|---|
| 1 | 0.4 |
| 2 | 3.0 |
| 3 | 2.8 |
| 4 | 0.6 |
| 5 | 3.0 |

When compared to other groups, based on the gross necropsy data, it is clear that there was markedly fewer and less substantial adhesions in Groups 1 and 4 (Test A and AlloDerm®, respectively); the only adhesions evident were in 2 of 5 animals in each of these groups with small areas of adhesion to the suture line but not to the article itself. Based on the gross adhesion scores Group 1 (Test A) exhibited the least substantial adhesions when compared to any other group. Groups 3 (Test C) and 5 (Prolene®) exhibited the most severe adhesions scores as compared to the other groups. These results were corroborated by statistical analyses that revealed significant differences among the Groups in adhesion amount and type scores which, when examined after dividing the Groups into two sets containing Groups 2, 3, and 5, and Groups 1 and 4, respectively. No statistically significant differences in adhesion amount or type scores were detected between Groups 2, 3, and 5, though all three of these groups had significantly higher mean scores than Groups 1 and 4. Similarly, no statistically significant differences in adhesion amount or type scores were detected between Groups 1 and 4, although both of these groups had significantly lower scores than Groups 2, 3, and 5.

Figure 6:
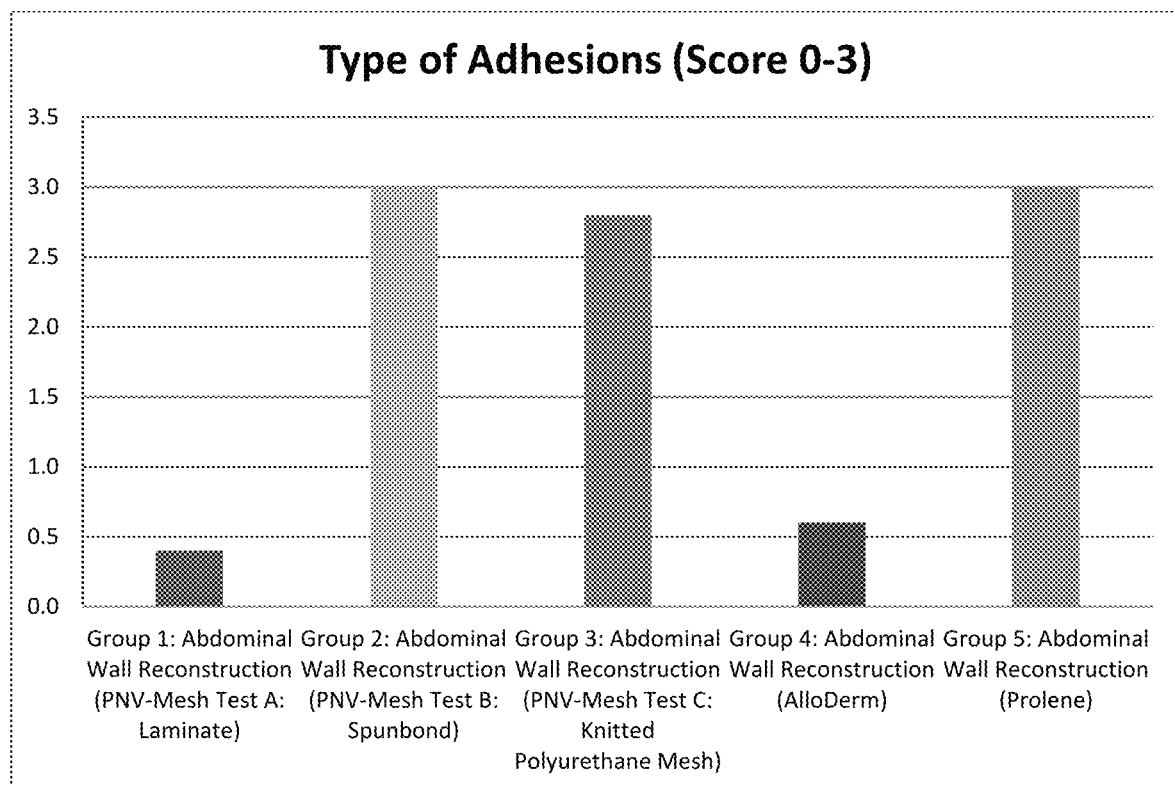
FIG. 6 is a bar chart illustrating results of adhesion type.

As shown in Table 10 and FIG. 6, Group 1 (Test A) exhibited the least shrinkage when compared to all other groups. Group 4 (AlloDerm®) showed the next least overall amount of shrinkage.

TABLE 10

| Group | Graft size (width cm) | Graft size (length cm) | Graft area (cm$^2$) |
|---|---|---|---|
| 1 | 3.2 | 6.7 | 21 |
| 2 | 3.0 | 6.5 | 19.5 |
| 3 | 3.1 | 6.1 | 19 |
| 4 | 3.1 | 6.6 | 20.5 |
| 5 | 2.9 | 6.2 | 18 |

Accordingly, the synthetic tissue repair laminate of the present disclosure performed exceptionally well, there being effectively no tissue adhesion to the barrier layer surface and no shrinkage of the laminate. Notably, while the barrier layer of the laminate, the spunbond and the warp knit were all formed from the same polyurethane resin, both the spunbond and the warp knit were highly adhesive to tissue and showed significant shrinkage in vivo.

The contents of all references, and published patents and patent applications cited throughout the application are hereby incorporated by reference. Those skilled in the art will recognize that the disclosure may be practiced with variations on the disclosed structures, materials, compositions and methods, and such variations are regarded as within the ambit of the disclosure.

Those skilled in the art will recognize, or be able to ascertain using no more than routine experimentation, many equivalents to the specific embodiments and methods described herein. Such equivalents are intended to be encompassed by the scope of the following claims.

It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

The invention claimed is:

1. A tissue repair laminate comprising:
   (a) a biodegradable polyurethane foam layer having first and second oppositely facing major surfaces; and
   (b) a thermoplastic, biodegradable polyurethane barrier layer having first and second oppositely facing major surfaces;
   wherein the first major surface of said barrier layer and the second major surface of said foam layer face each other;
   wherein said foam layer comprises a pore structure configured for cellular infiltration; and
   wherein the second major surface of said barrier layer is less adhesiogenic than the first major surface of said foam layer, and
   wherein the tissue repair laminate shrinks less than 20% in any single surface area, after 10 days under in vivo conditions.

2. A tissue repair laminate according to claim 1, wherein the foam layer polyurethane is thermoset.

3. A tissue repair laminate according to claim 1, wherein said tissue repair laminate shrinks less than 15%, in any single surface area, after 10 days under in vivo conditions.

4. A tissue repair laminate according to claim 1, wherein the foam layer has a thickness between about 0.1 mm and about 10 mm.

5. A tissue repair laminate according to claim 1, wherein the barrier layer has a thickness between about 20 μm and about 1000 μm.

6. A tissue repair laminate according to claim 1, wherein the average pore size of the polyurethane foam layer is greater than 50 μm.

7. A tissue repair laminate according to claim 1, wherein the polyurethane foam layer degrades, under the conditions of ASTM F1635, such that the mass of the foam layer decreases by between 10% and 90% in a period of one year or less.

8. A tissue repair laminate according to claim 1, wherein the polyurethane barrier layer degrades, under the conditions of ASTM F1635, such that the number average molecular weight ($M_n$) of the polyurethane decreases by between 10% and 90% in a period of one year or less.

9. A tissue repair laminate according to claim 1, wherein the polyurethane foam is derived from one or more biodegradable polyols, one or more isocyanates and, optionally, one or more non-biodegradable polyols.

10. A tissue repair laminate according to claim 9, wherein the biodegradable polyol comprises a polyester polyol.

11. A tissue repair laminate according to claim 10, wherein the polyether polyol is selected from one or more of glycerol ethoxylate, glycerol propoxylate, glycerol ethoxylate-co-propoxylate, glycerol ethoxylate-block-propoxylate, pentaerythritol ethoxylate, pentaerythritol propoxylate and trimethylolpropane propoxylate.

12. A tissue repair laminate according to claim 1, wherein the polyurethane barrier layer is derived from one or more polyols, one or more isocyanates and one or more chain extenders.

13. A tissue repair laminate according to claim 12, wherein the polyurethane barrier layer is derived from:
one or more chain extenders represented by formula (1) or formula (2)

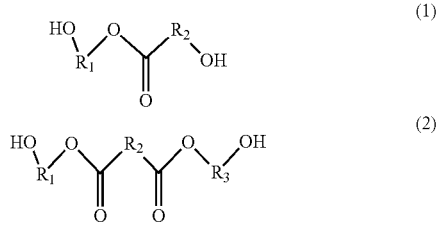

wherein $R_1$, $R_2$ and $R_3$ are independently selected from optionally substituted $C_{1-20}$ alkylene and optionally substituted $C_{2-20}$ alkenylene;
one or more aliphatic polyester polyols; and
one or more aliphatic diisocyanates.

14. A tissue repair laminate according to claim 13, wherein the barrier layer polyurethane comprises an oriented polyurethane.

15. A tissue repair laminate according to claim 14, wherein the barrier layer polyurethane comprises a biaxially oriented polyurethane.

16. A tissue repair laminate according to claim 14, wherein the oriented polyurethane is annealed.

17. A tissue repair laminate according to claim 1, wherein the polyurethane barrier layer has a number average molecular weight ($M_w$) up to 200,000 Daltons.

18. A tissue repair laminate according to claim 9, wherein the biodegradable or non-biodegradable polyols have a molecular weight of less than or equal to about 10,000 Daltons.

19. A tissue repair laminate according to claim 12, wherein the biodegradable or non-biodegradable polyols have a molecular weight of less than or equal to about 10,000 Daltons.

20. A tissue repair laminate according to claim 19, wherein the polyol comprises a polyester polyol.

21. A tissue repair laminate according to claim 20 wherein the polyester polyol is derived from one or more diol initiators and one or more hydroxy acids, diacids or cyclic esters and combinations thereof.

22. A tissue repair laminate according to claim 13, wherein the barrier layer polyurethane further comprises one or more aliphatic polyol chain extenders which are hydrolytically non-degradable under in vivo conditions.

23. A tissue repair laminate according to claim 22, wherein the aliphatic polyol chain extenders do not contain ester functionality in their backbones.

24. A tissue repair laminate according to claim 22, wherein the one or more aliphatic polyol chain extenders is an alkane diol having up to 30 carbon atoms.

25. A tissue repair laminate according to claim 13, wherein the aliphatic diisocyanate is selected from the group consisting of 4,4'-methylene dicylcohexyl diisocyanate (HMDI), 1,6-hexane diisocyanate (HDI), 1,4-butane diisocyanate (BDI), L-lysine diisocyanate (LDI), 2,4,4-trimethylhexamethylenediisocyanate, ethyl-L-lysine diisocyanate (ELDI), methyl-L-lysine diisocyanate (MLDI), and mixtures thereof.

26. A tissue repair laminate according to claim 13, wherein $R_1$, $R_2$ and $R_3$ of formulae (1) and (2) are independently selected from substituted $C_{1-6}$ alkylene and substituted $C_{2-6}$ alkenylene.

27. A tissue repair laminate according to claim 13, wherein the chain extender of formula (1) or formula (2) is selected from the group consisting of hydroxy-acetic acid 3-hydroxy-propyl ester, 6-hydroxy-hexanoic acid 2-hydroxyethyl ester, 6-hydroxy-hexanoic acid 4-hydroxybutyl ester, ethylene glycol succinic acid diester diol, ethylene glycol fumaric acid diester diol, glycolic acid-ethylene glycol dimer, lactic acid-ethylene glycol dimer and mixtures thereof.

28. A tissue repair laminate according to claim 13, wherein the polyurethane comprises hard and soft segments and wherein the hard segment content (% HS) of the polyurethane is between 2 to 100 wt. %.

29. A tissue repair laminate according to claim 27, wherein the polyurethane comprises hard and soft segments and wherein the soft segment content (% SS) of the polyurethane is at least 25%.

30. A tissue repair laminate according to any one of claim 28, wherein the polyurethane comprises hard and soft segments and wherein the hard segment content (% HS) of the polyurethane is less than 60%.

31. A tissue repair laminate according to any one of claim 28, wherein the non-degradable length of the hard segment has a molecular weight between 100 and 10,000 Daltons.

32. A method of effecting tissue repair using the tissue repair laminate according to claim 1.

33. A method of repair of tissue damage in a subject in need thereof, the method comprising surgically implanting a tissue repair laminate according to claim 13, into a site of the tissue damage in the subject.

34. A method according to claim 33, wherein the damage comprises, a hernia, a ventral abdominal wall hernia, a rotator cuff injury, a pelvic organ prolapse, or a uro-gynecological injury.

35. A method according to claim 33, wherein the site of the damage is a soft tissue, a mesenchymal tissue, an intraperitoneal tissue, a rotator cuff tissue, a pelvic tissue, or a uro-gynecological tissue.

36. A method of reinforcing tissues in surgical procedures, the method comprising surgically implanting a tissue repair laminate according to claim 1, into a site requiring tissue reinforcement.

37. A method according to claim 36, wherein the surgical procedure is abdominoplasty, breast reconstruction, midline closures, lateral closures, hernia repair, retrorectus hernia repair, Rives-Stoppa procedures, incisional hernias or cosmetic surgery.

* * * * *